United States Patent [19]

Nishihira et al.

[11] Patent Number: 5,811,573
[45] Date of Patent: Sep. 22, 1998

[54] PROCESS FOR PRODUCING A DIARYL CARNONATE

[75] Inventors: Keigo Nishihira; Shuji Tanaka; Yuki Nishida; Ii Hirofumi; Satoru Fujitsu; Katsumasa Harada; Ryoji Sugise; Koichi Kashiwagi; Takashi Doi, all of Ube, Japan

[73] Assignee: Ube Industries, Ltd., Ube, Japan

[21] Appl. No.: 988,759

[22] Filed: Dec. 11, 1997

Related U.S. Application Data

[62] Division of Ser. No. 814,089, Mar. 10, 1997, Pat. No. 5,731,453.

[30] Foreign Application Priority Data

Mar. 12, 1996 [JP] Japan .................................. 8-054971
Jun. 7, 1996 [JP] Japan .................................. 8-145849

[51] Int. Cl.⁶ .................................................. C07C 69/36
[52] U.S. Cl. ........................................................ 560/146
[58] Field of Search .............................................. 560/146

[56] References Cited

U.S. PATENT DOCUMENTS

| | | | |
|---|---|---|---|
| 3,471,549 | 10/1969 | Hulsmann et al. | 560/86 |
| 3,476,785 | 11/1969 | Huelsmann et al. | 560/146 X |
| 3,704,309 | 11/1972 | Roy | 560/146 X |
| 4,234,733 | 11/1980 | Isshiki et al. | 560/146 X |
| 4,451,664 | 5/1984 | Ranade | 560/146 X |
| 4,482,732 | 11/1984 | Ranade | 560/86 |
| 4,482,733 | 11/1984 | Ranade | 560/86 |

*Primary Examiner*—Michael G. Ambrose
*Attorney, Agent, or Firm*—Burgess, Ryan & Wayne

[57] ABSTRACT

A diaryl carbonate with a high degree of purity is produced at a high yield by (A) subjecting (a) a diaryl oxalate and a phenol compound or (b) an alkylaryl oxalate to transesterification reaction in one or two stages in the presence of a catalyst to prepare a diaryl oxalate, while removing a by-product from the reaction system; (B) collecting the diaryl oxalate from the resultant reaction product mixture of the step (A); (C) subjecting the diaryl oxalate to a decarbonylation reaction, preferably in the presence of a phosphorous compound-containing catalyst, to convert the diaryl oxalate to a corresponding diaryl carbonate, while removing a reaction by-product comprising carbon monoxide from the reaction system; and (D) collecting the diaryl carbonate from the reaction product mixture of the step (C).

14 Claims, 5 Drawing Sheets

STAGE (A-a)    STAGE (A-b)

PROCESS FOR PRODUCING A DIARYL CARNONATE

RELATED APPLICATIONS

This application is a divisional application of Ser. No. 08/814,089, filed Mar. 10, 1997, now U.S. Pat. No. 5,731,453, the entire contents of which are incorporated herein by reference.

BACKGROUND OF THE INVENTION

1. Field of the Invention

The present invention relates to a process for producing a diaryl carbonate. More particularly, the present invention relates to a process for producing a diaryl carbonate from (a) a dialkyl oxalate and a phenol compound and/or (b) an alkylaryl oxalate through a diaryl oxalate, with a high degree of purity and at a high yield.

The diaryl carbonate, for example, diphenyl carbonate, produced by the process of the present invention is an important material for producing polycarbonate resins.

2. Description of the Related Art

It is known that a diaryl carbonate, for example, diphenyl carbonate (DPC) can be produced by various conventional processes, for example, a non-halogen method in which a dialkyl carbonate is reacted with a phenol compound, or a phosgene method in which phosgene is reacted with a phenol compound, etc. These conventional processes are not satisfactory for industries due to the following reasons.

Namely, in the phosgene method for the diaryl carbonate, phosgene is a strong poisonous substance and thus must be very carefully handled, and the reaction of phosgene with the phenol compound needs a large amount of an alkali. Also, this reaction causes the resultant reaction product mixture to contain, in addition to the target diaryl carbonate, a certain amount of halogen-containing compounds, and the removal of the halogen-containing compounds from the reaction product mixture is significantly difficult as described in Japanese Examined Patent Publication No. 58-50977.

Also, the non-halogen methods for producing the diaryl carbonate include a method as disclosed in Japanese Unexamined Patent Publication No. 3-291,257 and No. 4-211,038, in which the diaryl carbonate is produced by a transesterification reaction of a dialkyl carbonate with a phenol compound; and a method as disclosed in Japanese Unexamined Patent Publication No. 4-9,358, in which an alkylaryl carbonate is subjected to a disproportionation reaction.

The method of producing the diaryl carbonate by a transesterification reaction of the dialkyl carbonate with the phenol compound is disadvantageous in that the rate of the transesterification reaction, especially from the dialkyl carbonate into a corresponding alkylaryl carbonate is low. Accordingly, to eliminate this disadvantage, various special catalyst or complicated production processes or apparatuses have been provided as disclosed in Japanese Unexamined Patent Publication No. 4-235,951 and No. 4-224,547.

Also, the method of producing the diaryl carbonate by a disproportionation reaction of a corresponding alkylaryl carbonate is disadvantageous in that since the alkylaryl carbonate is an intermediate product of the transesterification reaction from the dialkyl carbonate into a corresponding diaryl carbonate, and the resultant reaction product mixture contains, in addition to the alkylaryl carbonate, various compounds and non-reacted starting compounds, the target alkylaryl carbonate is significantly difficult to isolate from the reaction product mixture and to produce or obtain in an industrial scale. Therefore, the disproportionation method is quite unsatisfactory for industrial utilization.

Separately, for the production of a diaryl oxalate, various methods are known. For example, Japanese Examined Patent Publication No. 52-43,826 discloses a diaryl oxalate-production method by a direct esterification reaction of oxalic acid with a phenol compound in an organic solvent in the presence of an esterification catalyst at an elevated temperature of 100° to 130° C., and Japanese Examined patent Publication No. 56-8,019 and Japanese Unexamined patent Publication No. 49-42,621 disclose a diaryl oxalate ester-production method by a transesterification reaction of a dialkyl oxalate with a diaryl carbonate. Also, Japanese Examined Patent Publication No. 56-2,541 and No. 57-47,658 disclose a method of producing a diaryl oxalate by a transesterification reaction of dialkyl oxalate with an aryl ester of a lower fatty acid.

The diaryl oxalate-production method by the direct esterification reaction of oxalic acid with a phenol compound is disadvantageous in that the reaction rate is very low and thus a very long time is needed to complete the reaction, and thus this method is unsatisfactory from the point of view of the industry. Also, the diaryl oxalate-production method by a reaction of a dialkyl oxalate with a diaryl carbonate or an aryl ester of a lower fatty acid is disadvantageous in that the resultant reaction product mixture contains, in addition to the target diaryl oxalate, various by-products, and thus complicated or intricate refining steps are necessary to isolate the diaryl oxalate. Also, as mentioned above, the diaryl carbonate is not produced on an industrial scale and thus is difficult to obtain commercially. Therefore this method is not satisfactory for industry.

Further separately, with respect to a decarbonylation reaction of diphenyl oxalate, "Organic Synthetic Chemistry, Vol. 5, Report 4, 1948, "Thermodecomposition of diphenyl esters of dicarboxylic acid (Second Report)", reported that diphenyl carbonate could be obtained by a thermal decomposition of diphenyl oxalate at a high temperature. However, this method is unsatisfactory in that the yield of diphenyl carbonate is low, because phenol and carbon dioxide are produced as by-products.

Also, U.S. Pat. No. 4,544,507 for P. Foley discloses a method of producing a carbonate diester by heating an oxalate diester in a solvent in the presence of an alkali metal alcoholate at a temperature of 50° to 150° C. This U.S. patent, however, states only that when diphenyl oxalate was subjected, as an oxalate diester, to the above-mentioned catalytic method, the resultant product comprised, as a principal component, the diphenyl oxalate which was the starting compound. Also, the U.S. patent is quite silent as to the production of dipheyl carbonate from the diphenyl oxalate. Further, the U.S. patent does not concretely disclose a method of producing diphenyl oxalate. Namely, the U.S. patent includes no suggestion of the production of a diaryl oxalate from a combination of a dialkyl oxalate with a phenol compound or alkylaryl oxalate by a transesterification reaction.

SUMMARY OF THE INVENTION

An object of the present invention is to provide a process for producing a diaryl carbonate with a high degree of purity at a high yield.

Another object of the present invention is to provide a process for producing a diaryl carbonate with simple and easy procedures without using poisonous or harmful materials and complicated or intricate procedures.

Still another object of the present invention is to provide a process for producing a diaryl carbonate from a starting material comprising (a) a combination of a dialkyl oxalate with a phenol compound and/or (b) a alkylaryl oxalate with a high efficiency.

The above-mentioned objects can be attained by the process of the present invention for producing a diaryl carbonate, which comprises the steps of:

(A) subjecting a starting material comprising at least one member selected from the group consisting of
- (a) combinations of a dialkyl oxalate with a phenol compound, and
- (b) alkylaryl oxalates to a transesterification reaction in the presence of a transesterification catalyst to prepare a diaryl oxalate, while removing a reaction by-product from the reaction system of the step (A);

(B) collecting the diaryl oxalate from the resultant reaction product mixture of the step (A);

(C) subjecting the collected diaryl oxalate to a decarbonylation reaction to convert the diaryl oxalate to a corresponding diaryl carbonate and carbon monoxide, while removing the carbon monoxide from the reaction system of the step (C); and (D) collecting the diaryl carbonate from the resultant reaction product mixture of the step (C).

In an embodiment of the process of the present invention, the step (A) is carried out in two stages consisting of (A-a) a first stage in which the dialkyl oxalate and the phenol compound are subjected to a first transesterification reaction in the presence of a transesterification catalyst, while removing a resultant reaction by-product comprising a corresponding alkyl alcohol from the reaction system of the stage (A-a); and (A-b) a second stage in which the resultant reaction product mixture of the stage (A-a) containing the transesterification catalyst is subjected to a second transesterification reaction to provide a corresponding diaryl oxalate, while removing a resultant reaction by-product comprising a corresponding dialkyl oxalate.

DESCRIPTION OF THE PREFERRED EMBODIMENTS

Figure 1:
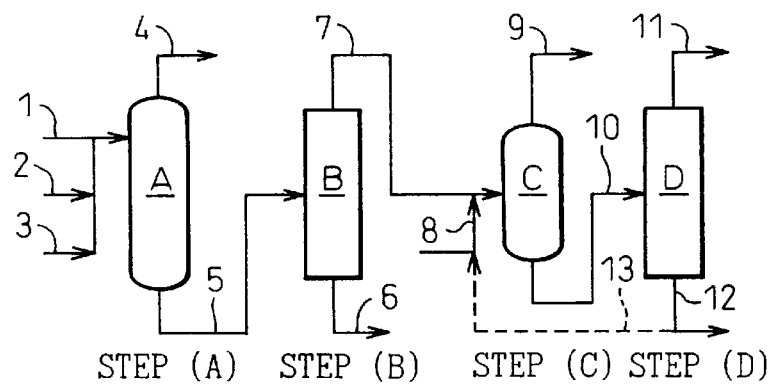
FIG. 1 is a flow sheet showing an embodiment of the process of the present invention.

The inventors of the present invention have carefully searched for a process for producing a diaryl carbonate with a high degree of purity at a high yield, and as a result, found that a dialkyl oxalate can be converted to a diaryl carbonate through a preparation of a diaryl oxalate and a decarbonylation of the diaryl oxalate. The present invention was completed on the basis of the finding.

In the process of the present invention, the step (A) comprises a transesterification reaction of (a) a combination of a dialkyl oxalate with a phenol compound in the presence of a transesterification reaction to provide a corresponding diaryl oxalate and a simultaneous removal of a reaction by-product from the reaction system of the step (A); the step (B) comprises a collection of the diaryl oxalate from the resultant reaction product mixture of the step (A); the step (C) comprises a decarbonylation reaction of the collected diaryl oxalate to convert it to a corresponding diaryl carbonate and carbon monoxide, and a simultaneous removal of the carbon monoxide from the reaction system of the step (C); and the step (D) comprises a collection of the diaryl carbonate from the resultant reaction product mixture of the step (C).

In the process of the present invention, the step (A) can be carried out in two stages. Namely, in a first stage (A-a), a combination of a dialkyl oxalate and a phenol compound is subjected to a first transesterification reaction in the presence of a transesterification catalyst, while removing a resultant by-product comprising a corresponding alkyl phenol from the reaction system of the stage (A-a); and then in a second stage (A-b), the resultant reaction product mixture of the stage (A-a) containing the transesterification catalyst is subjected to a second transesterification reaction to provide a corresponding diaryl oxalate, while removing a resultant reaction by-product comprising a corresponding dialkyl oxalate.

The process of the present invention includes the following reactions.

Reaction (I):

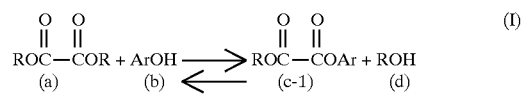

Reaction (II):

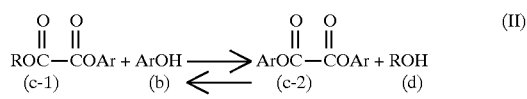

Reaction (III):

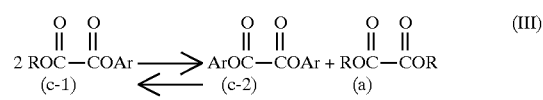

Reaction (IV):

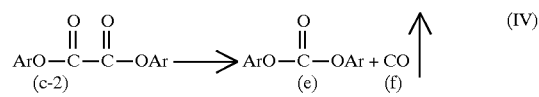

In the above-mentioned reaction formulae, R represents an alkyl group and Ar represents an aryl group.

When a dialkyl oxalate (a) and a phenol compound (b) are subjected to a reaction (I), namely a first transesterification reaction, a corresponding alkyl aryl oxalate (c-1) and a by-product consisting of a corresponding alkyl alcohol (d) are produced, and in Reaction (II), the alkylaryl oxalate (c-1)

reacts with the phenol compound (b) reacts with the phenol compound (b) to produce a diaryl oxalate (c-2) and a by-product consisting of a corresponding alkyl alcohol (d).

In Reaction (III), namely a second transesterification reaction, an alkylaryl oxalate (c-1) supplied as a starting material to the step (A), or produced by the reaction (I) in the first stage (A-a) of the step (A) is subjected to a transesterification reaction and converted to a corresponding diaryl oxalate (c-2) and a by-product consisting of dialkyl oxalate (a).

In this reaction, the second transesterification reaction is also referred to as a disproportionation reaction. Namely, the term "transesterification reaction" used in the process of the present invention includes a disproportionation reaction of an alkylaryl oxalate into corresponding diaryl oxalate and dialkyl oxalate.

In reaction (IV), the diaryl oxalate (c-2) is decarbonylated into a corresponding diaryl carbonate (e) and a by-product consisting of carbon monoxide (f).

In reactions (I) and (II), the productions of the alkylaryl oxalate (c-1) and the diaryl oxalate (c-2) are promoted by removing the by-product consisting of the alkyl alcohol (d). Also, in Reaction (III), the removal of the by-product consisting of the dialkyl oxalate (a) promotes the production of the diaryl oxalate.

As mentioned above, when a dialkyl oxalate and a phenol compound are subjected to the step (A) in a single stage, reactions (I) (II) and (III) concurrently occur. When the step (A) is carried out in two stages (A-a) and (A-b), in the first stage (A-a), mainly the transesterification reaction (I) of a dialkyl oxalate with a phenol compound occurs to prepare a corresponding alkylaryl oxalate and an alkyl alcohol, and concurrently reactions (II) and (III) occur to a small extent to produce a corresponding diaryl oxalate, dialkyl oxalate and alkyl alcohol. Also, in the second stage (A-b), the transesterification (disproportionation) reaction(III) of the alkylaryl oxalate occurs as a main reaction. Also, the second stage (A-b) optionally includes, to a small extent, reactions (I) and (II). Therefore, the main product of the stage (A-b) is diaryl oxalate and the main by-product is dialkyl oxalate.

When the starting material of the step (A) is an alkylaryl oxalate, the transesterification (disproportionation) reaction (III) occurs to produce diaryl oxalate and dialkyl oxalate. In industry, the alkylaryl oxalate is preferably supplied by reaction (I). Therefore, in the step (A) of the process of the present invention, the reactions of the stage (A-a) and the stage (A-b) may be carried out concurrently or in the order of reaction (I) and then reactions (II) and (III). Preferably, the step (A) of the process of the present invention includes the stage (A-a) in which the dialkyl oxalate is converted to the corresponding alkylaryl oxalate by reaction (I), and the stage (A-b) in which the alkylaryl oxalate is converted to the corresponding diaryl oxalate by reaction (III).

In the step (A) of the process of the present invention, by-products, namely the alkyl alcohol and dialkyl oxalate can be substantially completely removed from the reaction system, and substantially no by-products other than alkyl alcohol and dialkyl oxalate are generated. Therefore, the reaction product mixture from the step (A) contains very small amounts of by-products, and thus in the step (B) the diaryl oxalate with a very high degree of purity can be collected at a very high yield from the reaction product mixture of the step (A) by a certain collecting procedure, for example, a distillation procedure.

When diphenyl oxalate is produced in the step A by the transesterification reaction of dialkyl oxalate with phenol, and the resultant reaction product mixture of the step (A) contains an excessive amount of non-reacted phenol in addition to the target diphenyl oxalate, the diphenyl oxalate reacts with phenol so as to form a crystalline adduct of diphenyl oxalate with phenol in a molar ratio of 1:2. Therefore, diphenyl oxalate can be collected in the form of a crystalline adduct with phenol by cooling the reaction product mixture of the step (A) so as to allow the adduct to crystallize. The crystalline adduct of diphenyl oxalate with phenol has a melting temperature of 101° to 103° C. and can be returned to diphenyl oxalate by heating the adduct at a temperature equal to or higher than the melting temperature of the adduct so as to release phenol. Therefore, diphenyl oxalate can be recovered from the diphenyl oxalate-phenol adduct by distillating the adduct at the melting temperature of the adduct or more so as to remove the released phenol.

In the step (C) of the process of the present invention, the target diaryl carbonate is produced at a high selectivity by the decarbonylation reaction (IV) of diaryl oxalate. In the step (C), carbon monoxide is produced as a by-product and other by-products are produced in a very small amounts. Therefore, in the step (D), the target diaryl carbonate with a high degree of purity can be collected at a high yield.

Figure 2:
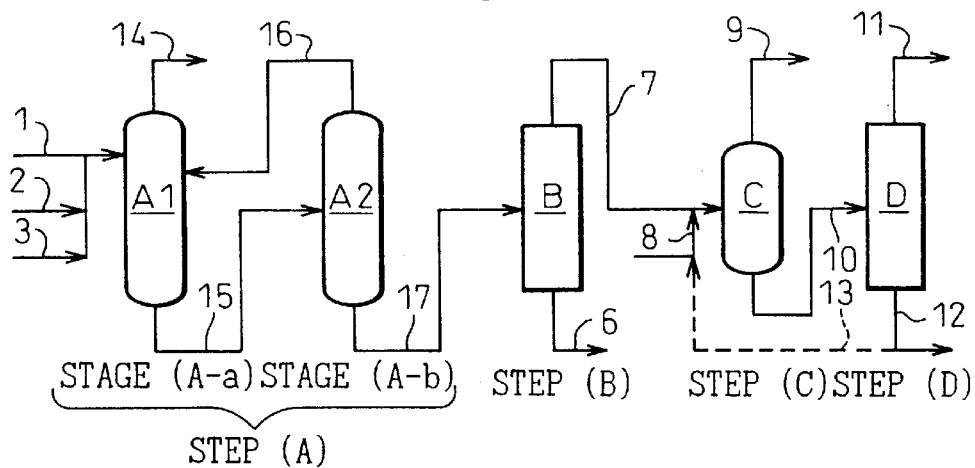
FIG. 2 is a flow sheet showing another embodiment of the process of the present invention.
Figure 3:
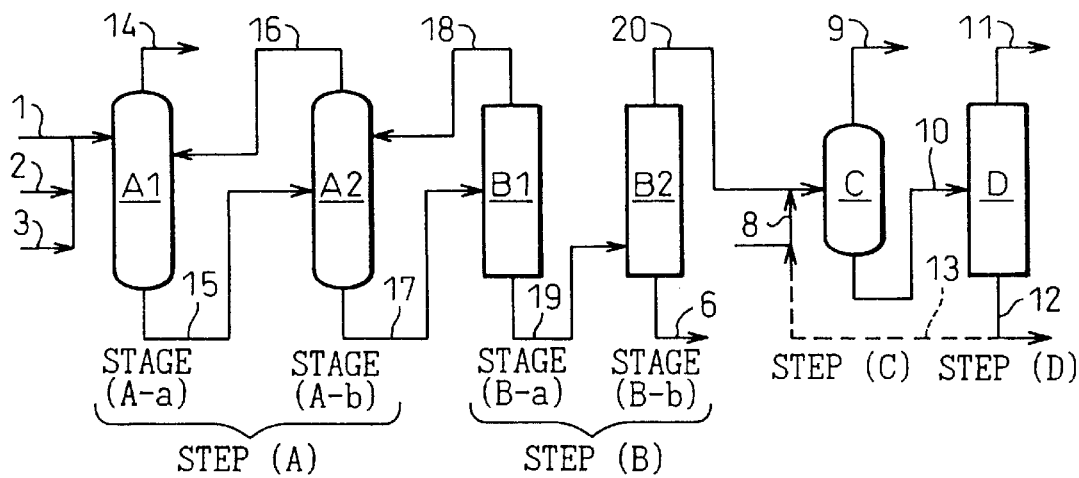
FIG. 3 is a flow sheet showing still another embodiment of the process of the present invention.
Figure 4:
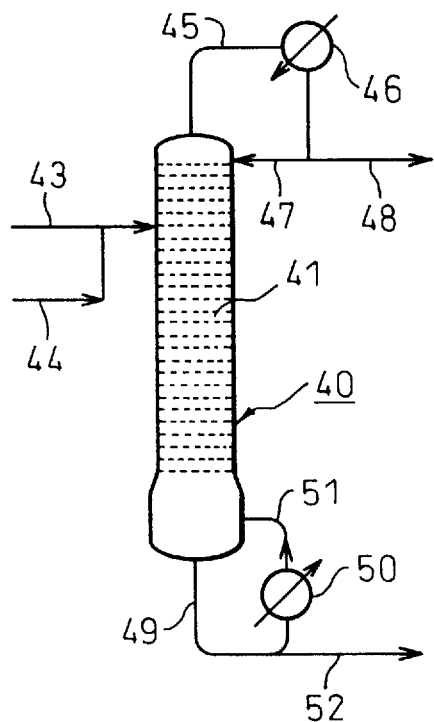
FIG. 4 is an explanatory cross-sectional view of an embodiment of the reaction apparatus for carrying out the step (A) of the process of the present invention.
Figure 5:
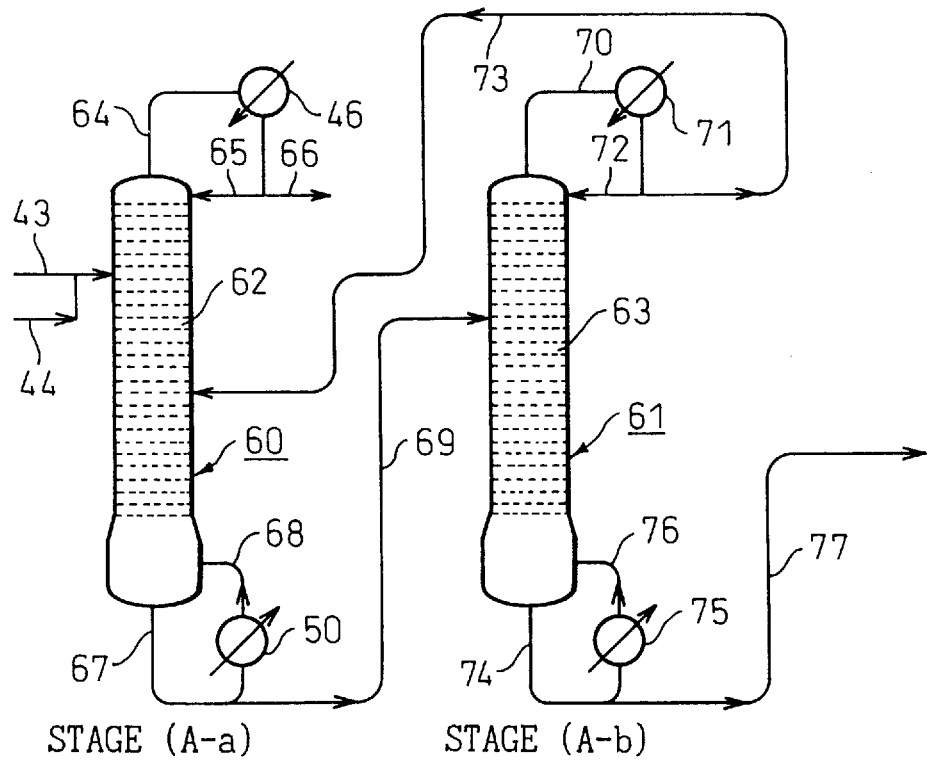
FIG. 5 is an explanatory cross-sectional view of another embodiment of the reaction apparatus for carrying out the step (A) of the process of the present invention.

FIGS. 1, 2 and 3 indicate flow sheets of various embodiments of the process of the present invention, and FIGS. 4 and 5 indicate certain embodiments of the apparatus for the step (A) of the process of the present invention.

In FIG. 1, a dialkyl oxalate, a phenol compound and a transesterification catalyst are supplied respectively through conduits 1, 2 and 3 into a transesterification reactor A for the step (A); the dialkyl oxalate is reacted with the phenol compound in the presence of the transesterification catalyst in the reactor A by the above-mentioned reactions (I), (II) and (III) while withdrawing a gas phase by-product comprising an alkyl alcohol from the reactor A through a conduit 4 connected to a top portion of the reactor A; and then a liquid phase reaction product mixture comprising the target diaryl oxalate and the esterification catalyst is withdrawn from the rector A through a conduit 5 connected to a bottom portion of the reactor A.

When the starting material consists of an alkylaryl oxalate, the alkylaryl oxalate and a transesterification (disproportionation) catalyst are supplied respectively through the conduits 1 and 3 into the reactor A; the alkylaryl oxalate is converted to a corresponding diaryl oxalate in the reactor A, while a resultant gas phase by-product comprising a corresponding dialkyl oxalate from the reactor A is withdrawn through the conduit 4; and then the liquid phase reaction product mixture containing the diaryl oxalate and the catalyst is withdrawn from the reactor A through the conduit 5.

The reaction product mixture of the step (A) is fed into a separator B for the step (B) through the conduit 5, and in the separator B, the impurities, for example, by-products, the non-reacted starting material and the catalyst are removed from the reaction product mixture in the separator B by means of, for example, a distillation or crystallization, and withdrawn from the separator B through a conduit 6 connected to a bottom portion of the separator B; and a remaining gas phase fraction comprising diaryl oxalate is, after optional refining, withdrawn from the separator B through a conduit 7 connected to the top portion of the separator B.

The diaryl oxalate containing fraction is fed into a decarbonylation reactor C through the conduit 7, optionally after being mixed with a decarbonylation catalyst supplied through a conduit 8, and subjected to a decarbonylation reaction in the reactor C, while withdrawing a gas phase by-product fraction comprising carbon monoxide from the reactor C through a conduit 9 connected to a top portion of the reactor C. Also, a resultant liquid phase fraction comprising diaryl carbonate is withdrawn from the rector C through a conduit 10 connected to the bottom portion of the reactor C.

The withdrawn liquid phase fraction of the step (C) is fed into a refining apparatus D, for example, a distiller, for the step (D) through the conduit 10, and the target diaryl oxalate is collected from the fraction in the refining apparatus D and delivered as a gas fraction from the refining apparatus D through a conduit 11 connected to the top portion of the refining apparatus D. A remaining liquid fraction containing the decarbonylation catalyst is withdrawn from the refining apparatus D through a conduit 12 connected to a bottom portion of the apparatus D. Optionally, all or a portion of the withdrawn liquid fraction of the step (D) is recycled into the decarbonylation reactor C through conduits 13, 8 and 7, and reused in the step (C).

In the embodiment of the process of the present invention is indicated in FIG. 2, the step (A) is carried out in two stages (A-a) and (A-b).

In FIG. 2, a dialkyl oxalate, a phenol compound and a transesterification catalyst are fed respectively through conduits 1, 2 and 3 into a first transesterification reactor A1, and the transesterification reaction (I) of dialkyl oxalate with the phenol compound in the presence of the transesterification catalyst is mainly carried out in the reactor A1, to produce a corresponding alkylaryl oxalate and a by-product comprising an alkyl alcohol. Also, in the reactor A1 for the first stage (A-a), the transesterification reaction (II) of the alkylaryl oxalate with the phenol compound and the transesterification (disproportionation) reaction of alkylaryl oxalate occur to a small extent to produce, as a principal product, a diaryl oxalate and as by-products, an alkyl alcohol and a dialkyl oxalate.

In the stage (A-a), the resultant gas phase fraction comprising the by-products is withdrawn from the first reactor A1 through a conduit 14 connected to a top portion of the first reactor A1, and the resultant liquid phase fraction comprising the alkylaryl oxalate, the transesterification catalyst and non-reacted starting material is withdrawn from the first reactor A1 through a conduit 15 connected to a bottom portion of the first reactor A1.

Then, the withdrawn liquid phase fraction from the first rector A1 is fed into a second transesterification (disproportionation) reactor A2 for the second stage (A-b), and is subjected to a second transesterification (disproportionation) reaction in the presence of the transesterification catalyst, to produce the diaryl oxalate and a by-product comprising the dialkyl oxalate and optionally the alkyl alcohol. The resultant gas phase fraction containing the by-product comprising dialkyl oxalate and optionally alkyl alcohol and non-reacted alkylaryl oxalate and phenol compound is withdrawn from the second reactor A2 through a conduit 16 connected to a top portion of the second reactor A2, and recycled into the first reactor A1 and reused for the first transesterification reaction in the first stage (A-a). Also, the resultant liquid phase fraction comprising the diaryl oxalate ester is withdrawn from the second rector A2 through a conduit 17 connected to the bottom portion of the second reactor A2, and fed into the separator B. Then, the same procedures as those in FIG. 1 are carried out in the separator B. the decarbonylation reactor C and the refining apparatus D.

In the embodiment of the process of the present invention indicated in FIG. 3, the step (A) is carried out in the same two stage procedures as in FIG. 2, the step (B) for collecting the diaryl oxalate is carried out in two stages (B-a) and (B-b), and the steps (C) and (D) are carried out by the same procedures as in FIGS. 1 and 2.

In FIG. 3, the liquid phase reaction product mixture withdrawn from the bottom portion of the second reactor A2 through the conduit 17 is fed into a first separator B1 wherein the diaryl oxalate is collected from the reaction product mixture. The resultant gas phase fraction is withdrawn from the first separator B1 through a conduit 18 connected to the top portion of the second separator B1 and recycled into the second reactor A2. Also, the resultant liquid phase fraction containing the diaryl oxalate is withdrawn from the first reactor B1 through a conduit 19 connected to the bottom portion of the first separator B1 and then fed into a second separator (refiner) B2.

The first separator B1 can be selected from various types of separators. For example, the first separator B1 is a crystallization separator in which the liquid phase reaction product mixture delivered from the step (A) is cooled to precipitate a resultant crystalline adduct of a diaryl oxalate, for example, diphenyl oxalate, and a phenol compound, for example, phenol, the precipitated crystalline adduct is separated and collected from the reaction product mixture, the collected crystalline adduct is heated to release phenol from the adduct, and the released phenol is evaporated away to leave the separated diaryl oxalate.

Alternatively, the separator B1 is a distillation separator wherein the liquid phase reaction product mixture is treated by a combination of an evaporator and a distiller or by a plurality of distillers to successively separate light ends (low boiling temperature substances) from heavy ends (high boiling temperature substances), and to collect a refined diaryl oxalate fraction.

The second separator (refiner) B2 is preferably a multi-step distiller in which the refined liquid phase fraction delivered from the first separator B1 is further refined by distillation.

The resultant gas phase fraction containing the refined diaryl oxalate is withdrawn from the second separator B2 through a conduit 20 connected to the top portion of the second separator B2 and transported into the decarbonylation step (C) and then into the collection step (D) in the same manner as in FIGS. 1 and 2.

The resultant liquid phase fraction containing the transesterification catalyst is withdrawn from the second separator B2 through the conduit 6 connected to the bottom portion of the second separator B2.

In the step (A) of the process of the present invention, a dialkyl oxalate and a phenol compound is subjected to a transesterification reaction in the presence of a transesterification catalyst while discharging a by-product containing a corresponding alkyl alcohol from the reaction system to outside thereof. In this transesterification reaction, the molar ratio of the dialkyl oxalate with the phenol compound is variable in response to the type and amount of the transesterification catalyst and the reaction conditions. Usually, the phenol compound is used preferably in a molar amount of 0.01 to 1000 times, more preferably 0.1 to 100 times, still more preferably 0.5 to 20 times, the molar amount of the dialkyl oxalate fed, as a starting material, to the step (A).

The amount of the transesterification catalyst to be fed into the step (A) of the process of the present invention is variable depending on the type of the catalyst, the type and scale of the reactor (for example, a multistep type distiller), the type and composition of the starting material and the transesterification reaction conditions. Usually, the transesterification catalyst is employed preferably in an amount of 0.0001 to 50% by weight, more preferably 0.001 to 30% by weight, still more preferably 0.005 to 10% by weight, based on the total weight of the starting material(for example, a combination of a dialkyl oxalate with a phenol compound).

In the step (A), the transesterification reaction is carried out preferably at a temperature at which the starting material and the resultant reaction products are in the state of a liquid (melt), and the reaction products such as an alkylaryl oxalate and diaryl oxalate are not thermally decomposed. Usually, the transesterification reaction in the step (A) is carried out at a temperature of preferably 50° to 350° C., more preferably 100° to 300° C., still more preferably 120° to 280° C.

The first transesterification reaction in the first stage (A-a) of the step (A) can be carried out under a reduced pressure, the ambient atmospheric pressure or an increased pressure. Preferably, the reaction pressure is adjusted to a level under which the resultant by-product containing an alkyl alcohol can be evaporated.

For example, when the reaction temperature is in the range of from 50° to 350° C., the reaction pressure in the first stage (A-a) of the step (A) is preferably in the range of from 0.001 mmHg (133.32 mPa) to 200 kg/cm$^2$ (19.6133 MPa), more preferably 0.01 mmHg (1333.2 mPa) to 100 kg/cm$^2$ (9.8067 MPa), still more preferably 0.1 mmHg (13332 mPa) to 50 kg/cm$^2$ (4.9034 MPa). The reaction time can be adjusted in response to the reaction temperature and pressure. Usually, the total reaction time of the first stage (A-a) of the step (A) is preferably 0.001 to 50 hours, more preferably 0.01 to 10 hours, still more preferably 0.02 to 5 hours.

In the first stage (A-a) of the step (A), the first transesterification reaction is carried out at a temperature of preferably 50° to 350° C., more preferably 100° to 300° C., still more preferably 120° to 280° C under a pressure of preferably 0.001 mmHg to 200 kg/cm$^2$, more preferably 0.01 mmHg to 100 kg/cm$^2$, still more preferably 0.1 mmHg to 50 kg/cm$^2$ for a reaction time of, preferably 0.001 to 50 hours, more preferably 0.01 to 10 hours, still more preferably 0.02 to 5 hours.

The dialkyl oxalate usable as a starting compound for the step (A) of the process of the present invention is preferably selected from those in which each alkyl group has 1 to 10 carbon atoms, more preferably 1 to 6 carbon atoms, still more preferably 1 to 4 carbon atoms. The dialkyl oxalate preferably includes dimethyl oxalate, diethyl oxalate, dipropyl oxalate, dibutyl oxalate, dihexyl oxalate, dioctyl oxalate, and methylethyl oxalate.

The dialkyl oxalates in which each alkyl group has 1 to 4 carbon atoms are advantageously used for the process of the present invention, because the alkyl alcohol generated as a by-product of the transesterification reaction can be easily removed by evaporation. Thus, the dialkyl oxalate is advantageously selected from dimethyl oxalate, diethyl oxalate, dipropyl oxalate and dibutyl oxalate.

The phenol compound usable as a starting compound for the step (A) of the process of the present invention, is preferably selected from phenol and substituted phenols with at least one substituent selected from the group consisting of alkyl groups having 1 to 6 carbon atoms, alkoxyl groups having 1 to 6 carbon atoms, a nitro group and halogen atoms. A most preferable phenol compound is unsubstituted phenol.

The substituted phenols include, for example, alkyl phenols, for example, o-, m- and p-cresols, xylenols (dimethylphenols), ethylphenols, methylethylphenols, propylphenols, butylphenols, hexylphenols, dipropylphenols, trimethylphenols, and tetramethylphenols; alkoxylphenols, for example, o-, m-and p-hydroxyphenol, and ethoxyphenols; halophenols, for example, p-chlorophenol and 3,5-dibromophenol; and nitrophenols, for example, o-, m- and p-nitrophenols.

When an alkylaryl oxalate is fed as a starting material into the step (A) of the process of the present invention, or in the second stage (A-b) of the step (A) in which the liquid phase fraction delivered from the first stage (A-a) is subjected to a second transesterification (disproportionation) reaction, the alkylaryl oxalate is converted to the corresponding diaryl oxalate and dialkyl oxalate. The amount of the transesterification catalyst is variable in response to the type of the catalyst, the type and scale of the reaction apparatus and the reaction conditions. Usually, the transesterification catalyst is used preferably in an amount of 0.0001 to 50% by weight, more preferably 0.001 to 30% by weight, still more preferably 0.005 to 10% by weight, based on the amount in weight of the alkylaryl oxalate.

The conditions for the transesterification (disproportionation) reaction of the alkylaryl oxalate are not limited to specific conditions. Preferably, the transesterification (disproportionation) reaction of the alkylaryl oxalate is carried out at a temperature of 50° to 350° C. under a pressure of 0.001 mmHg to 200 kg/cm$^2$ for a reaction time of 0.001 to 100 hours.

The alkylaryl oxalate usable for the process of the present indention is preferably selected from those in which the alkyl group has 1 to 10 carbon atoms and the aryl group is selected from an unsubstituted phenyl group and substituted phenyl groups having at least one substituent selected from alkyl groups with 1 to 6 carbon atoms, alkoxyl grounds with 1 to 6 carbon atoms, a nitro group and halogen atoms.

The alkylaryl oxalate may be selected from alkylphenyl oxalates, for example, methylphenyl oxalate, ethylphenyl oxalate, propylphenyl oxalate, butylphenyl oxalate, hexylphenyl oxalate, pentylphenyl oxalate and octylphenyl oxalate; and alkyl (substituted phenyl) oxalates, for example, methyl(p-methylphenyl)oxalate, methyl(p-ethylphenyl)oxalate, ethyl(p-methylphenyl)oxalate, ethyl(p-ethylphenyl)oxalate, ethyl (p-methyl (p-methoxyphenyl) oxalate, methyl(p-ethoxyphenyl)oxalate, methyl(p-nitrophenyl)oxalate, methyl (p-methyl (p-chlorophenyl) oxalate. Among the above-mentioned compounds, lower-alkylaryl oxalate having a lower alkyl group with 1 to 4 carbon atoms and an unsubstituted phenyl group are advantageously employed. This type of alkylaryl oxalates include methylphenyl oxalate, ethylphenyl oxalate, propylphenyl oxalate and butylphenyl oxalate.

The resultant diaryl oxalate from the step (A) or the stage (A-b) of the step (A) is preferably selected from diphenyl oxalate, di(p-methylphenyl)oxalate, di(p-methoxyphenyl) oxalate, di(p-nitrophenyl)oxalate, and di(p-chlorophenyl) oxalate. Most preferably diaryl oxalate is diphenyl oxalate.

The transesterification catalyst usable for the step (A) or the stage (A-a) of the step (A) is not limited to a specific group of compounds, as long as the catalyst is contributory to accelerating the transesterification reaction of the dialkyl oxalate to prepare the alkylaryl oxalate and/or diaryl oxalate.

Also, the transesterification catalyst usable for the stage (A-b) of the step (A) is not limited to a specific group of compounds, as long as the catalyst is contributory to promoting the transesterification (disproportionation) reaction of the alkylaryl oxalate to convert it to the diaryl oxalate. When the step (A) is carried out in two stages (A-a) and (A-b), the transesterification catalyst for the stage (A-a) may be te same as or different from the transesterification (disproportionation) catalyst for the stage (A-b). Preferably, from the point of view of industry, they are preferably the same as each other.

The transesterification catalyst usable for the stage (A-a) and/or the stage (A-b) may be selected from the conventional catalyst usable for the transesterfication reactions of dialkyl esters of dicarboxylic acids with phenol compounds. Also, the transesterification catalysts usable for the process of the present invention is preferably soluble in a reaction mixture of the dialkyl oxalate, the phenol compound, the alkylaryl oxalate and the diaryl oxalate.

In the step (A) of the present invention, the transesterification catalyst comprises at least one soluble compound selected from the group consisting of (1) Alkali metal compounds, cadmium compounds and zirconium compounds;
(2) lead compounds
(3) copper group metal compounds
(4) iron compounds
(5) zinc compounds
(6) organic tin compounds, and
(7) aluminum compounds, titanium compounds and vanadium compounds.

The alkali metal compounds, cadmium compounds and zirconium compounds (1) include lithium carbonate, dibutylamino-lithium, lithium acetylacetonate, cadmium diacetylacetonate, zirconium diacelylacetonate and zirconocene (bis($\eta$-cyclopentadienyl) zirconium (II)).

The lead compounds (2) include lead sulfide, lead hydroxide, plumbites, plumbates, lead carbonate, lead hydrogen carbonate, lead salts of organic acids, alkyl and aryl lead compounds (for example, tetrabutyl lead, tetraphenyl lead, triphenyl lead bromide and triphenyl lead), alkoxyl and aryloxy lead compounds (for example, dimethoxy lead, methoxylphenoxy lead and diphenoxy lead).

The copper group metal compounds (b) include copper compounds, for example, copper salts of organic acids (for example, copper acetate, copper diacetylacetonate and copper oleate), alkyl coppers (for example, butyl copper) alkoxyl coppers (for example, dimethoxy copper), copper halides (for example, copper chloride); and silver compounds, for example, silver nitrate, silver bromide and copper picrate.

The iron compounds (4) include iron hydroxide, iron carbonate, triacetoxy iron, trimethoxy iron, triethoxy iron and triphenoxy iron.

The zinc compounds (5) include zinc diacetylacetonate, diacetoxy zinc, dimethoxy zinc, diethoxy zinc and diphenoxy zinc.

The organic tin compounds (6) include tetraphenyltin ($Ph_4Sn$); acetoxy complexes of tin, for example, $Sn(OCOMe)_4$, $Bu_2Sn(OCOMe)_2$, $Me_3Sn(OCOMe)$, $Et_3Sn(OCOMe)$, $Bu_3Sn(OCOMe)$ and $Ph_3Sn-(OCOMe)$; alkoxy and aryloxy complexes of tin, for example, $Sn(OMe)_4$, $Sn(OEt)_4$, $Sn(OPh)_4$, $BU_2Sn(OMe)_2$, $Ph_2Sn(OMe)_2$, $Bu_2Sn(OEt)_2$, $Bu_2Sn(OPh)_2$, $Ph_3Sn(OEt)$, and $Et_3Sn(OPh)$; and $Me_3Sn(OCOPh)$, $Bu_2SnCl_2$, $Bu_2SnO$, $BuSnO(OH)$ and $Et_3SnOH$, $Ph_3SnOH$, wherein Ph represents a phenyl group, Me represents a methyl group, Et represents an ethyl group and Bu represents a butyl group.

The compounds (7) of aluminum, titanium and vanadium include aluminum compounds, for example, $Al_3$ (wherein X represents a halogen atom), $Al(OCOMe)_3$, $Al(OMe)_3$, $Al(OEt)_3$, $Al(OBu)_3$; $Al(OPh)_3$; compounds of titanium, for example, $TiX_3$, $Ti(OCOMe)_3$, $Ti(OMe)_3$, $Ti(OEt)_3$, $Ti(OBu)_3$, $Ti(OPh)_3$, $TiX_4$, $Ti(OCOMe)_4$, $Ti(OMe)_4$, $Ti(OEt)_4$, $Ti(OBu)_4$ and $Ti(OPh)_4$; and compounds of vanadium, for example, $VOX_3$, $VO(OCOMe)_3$, $VO(OMe)_3$, $VO(OEt)_3$, $VO(OPh)_3$ and $VX_5$.

The transesterification catalyst for the stages (A-a) and (A-b) of the step (A) advantageously comprises at least one member selected from the abovementioned lithium compounds, zirconium compounds, organic tin compounds, and titanium compounds more advantageously from the above-mentioned organic tin compounds and titanium compounds.

In the step (A) of the process of the present invention, a dialkyl oxalate is reacted with a phenol compound in the presence of a transesterification catalyst to prepare an alkylaryl oxalate and a by-product comprising an alkyl alcohol, and the alkylaryl oxalate is further reacted with the phenol compound and is disproportionated into a diaryl oxalate and a by-product comprising an alkyl alcohol and a dialkyl oxalate while removing the by-products from the reaction system. The reactions of the step (A) can be effected in any type of reactor which enables reactions (I), (II) and (III) to be carried out and the resultant by-products to be removed. A preferable reactor for the step (A) comprises at least one reactive distillation column, for example, a continuous multi-step reactive distillation column.

The multi-step reactive distillation column preferably has a theoretical plate number of at least two, more preferably 5 to 100, still more preferably 7 to 50. The multi-step reactive distillation column may be a multi-tray type distillation column having bubble cap trays, sieve trays, and valve trays or a packing type distillation column packed with fillers, for example, Rasching rings, Lessing rings or pole rings. Also, the reactive distillation column may have both the tray structure and packing structure.

The step (A) of the process of the present invention can be carried out by using a multi-step reactive distillation column as shown in FIG. 4. In FIG. 4, the multi-step reactive distillation column 40 is provided with a plurality of reactive distillation trays on which reactions (I), (II) and (III) or (II) and (III) are carried out and the resultant by-products having a low boiling temperature are evaporated. In FIG. 4, a mixture of a dialkyl oxalate with a phenol compound or an alkylaryl oxalate in the state of a liquid is fed into the column 40 through a conduit 43 and a catalyst is fed into the column 40 through a conduit 44. The resultant light ends containing the by-product are distilled and withdrawn in a gas phase from the top of the column 40 through a conduit 45, and cool-condensed by a cooler 46. A portion of the condensed fraction is recycled into the top portion of the column 40 through a conduit 47. The reflux ratio of the condensed fraction is preferably 0 to 20, more preferably 0 to 10. The remaining portion of the condensed fraction containing mainly an alkyl alcohol or dialkyl oxalate is preferably discharged to the outside of the column 40 through a conduit 48. In the reactive distillation column 40 of FIG. 4, the starting material and the catalyst are fed in liquid phase into an upper portion of the tray region especially between the center and the top of the tray region through the conduits 43 and 44. The mixture of the starting material and the catalyst flows down through the trays, while carrying out reactions (I), (II), and (III) or (II) and (III), the resultant liquid phase fraction containing the diaryl oxalate in a high concentration flows down into the bottom portion of the column, and the resultant gas phase fraction flows up through the trays so as to successively increase the concentration of the alkyl alcohol or dialkyl oxalate.

The resultant liquid phase fraction is withdrawn from the bottom portion of the column 40 through a conduit 49. A portion of the withdrawn liquid phase fraction is heated by a heater 50 and recycled into the column 40 through a conduit 51, to control the reaction temperature in the column 40 to a desired level. The remaining portion of the withdrawn liquid phase fraction is fed into the next step through a conduit 52.

The step (A) can be carried out in two stages (A-a) and (A-b) by using a reactive distillation apparatus shown in FIG. 5 and having a first reactive distillation column 60 for the first stage (A-a) and a second reactive distillation column 61 for the second stage (A-b) connected in series to the first column 60.

The first and second columns 60 and 61 have a plurality of reactive distillation trays 62 and 63.

In FIG. 5, a mixture of the starting material including a dialkyl oxalate and a phenol compound with a transesterification catalyst is fed into the first column 60 through conduits 43 and 44, to be subjected mainly to reaction (I) and optionally to reactions (II) and (III). The resultant gas phase fraction is withdrawn from the top portion of the first column 60 through a conduit 64 and cool-condensed by the cooler 46. A portion of the condensed portion is recycled into the top portion of the first column 60 through a conduit 65 and the remaining portion of the condensed fraction is discharged to the outside of the reaction system through a conduit 66. Also, a resultant liquid phase fraction is withdrawn from the bottom portion of the first column 60 through a conduit 67. A portion of the withdrawn liquid phase fraction is heated by a heater 50 and recycled into the first column 60 through a conduit 68 to control the reaction temperature of the first column 60 to a desired level. The remaining portion of the withdrawn liquid phase fraction is fed into the tray region 63 of the second reactive distillation column 61 through a conduit 69. The fed liquid phase fraction comprises an alkylaryl oxalate, the catalyst and the non-reacted dialkyl oxalate and phenol compound. Therefore, in the second column, the reaction (III) is mainly carried out in the presence of the transesterification (disproportionation) catalyst.

The fed liquid phase fraction flows down through a plurality of trays and the alkylaryl oxalate in this fraction is converted to a diaryl oxalate and a by-product containing a dialkyl oxalate, and separated into a liquid phase fraction comprising the target diaryl oxalate as a principal component, and a gas phase fraction.

The resultant liquid phase fraction flows down through the trays, while increasing the concentration of the diaryl oxalate therein, and reaches the bottom of the second column 61.

Also, the resultant gas phase fraction flows up through the trays, while increasing the concentration of the dialkyl oxalate therein and reaches the top of the second column 61.

The gas phase fraction contains the dialkyl oxalate in a high concentration and small amounts of alkylaryl oxalate and alkyl alcohol. This gas phase fraction is withdrawn from the top portion of the second column 61 through a conduit 70 and cool-condensed by a cooler 71. A portion of the condensed fraction is recycled at a reflux ratio of preferably 0 to 20, more preferably 0 to 10 into the top portion of the second column 61 through a conduit and the remaining portion of the condensed fraction is recycled into the middle portion of the first column 60 through a conduit 73. A portion of the remaining portion may be discharged to the outside of the reaction system.

The resultant liquid phase fraction containing, as a principal component, the diaryl oxalate is withdrawn from the bottom portion of the second column 61 through a conduit 74. A portion of the withdrawn liquid phase fraction is heated by a heater 75 and recycled into the second column 61 through a conduit 76, to control the reaction temperature of the second column 61 to a desired value. The remaining portion of the liquid phase fraction is fed into the next step through a conduit 77.

The first and second reactive distillation columns preferably have the theoretical plate number of 2 or more, more preferably 5 to 100, still more preferably 7 to 50.

Also, the first and/or second reactive distillation column may be a packing type distillation column.

In FIG. 5, the conduit 69 for feeding liquid phase fraction of the first column 60 into the second column 61 is preferably connected to an upper portion of the second column 61 so that the liquid phase fraction can be fed into a portion of the tray region 63 above the transverse center line of the region. In this case, the fed liquid phase fraction can flow down through the number of the trays large enough to complete the conversion of the alkylaryl oxalate to the diaryl oxalate.

In the second stage (A-b) of the step (A) of the process of the present invention, the reaction temperature of the liquid phase reaction product mixture fed from the first reactive distillation column 60 to the second reactive distillation column 61 is preferably controlled to a level not lower than the temperature at which the reactants and the reaction products can be maintained at the state of a solution and the alkylaryl oxalate and the diaryl oxalate do not thermally decompose. Usually, the reaction temperature is controlled to preferably 50° to 350° C., more preferably 100° to 300° C., still more preferably 120° to 280° C.

The reaction in the second stage (A-b) of the step (A) can be carried out under a reduced pressure, the ambient atmospheric pressure or an increased pressure. Preferably the reaction pressure is controlled to a level under which the resultant by-product comprising, as a main component, dialkyl oxalate can be evaporated and the resultant gas phase fraction can be discharged from the reaction system. For example, when the reaction of the second stage (A-b) is carried out at a temperature of from 50° to 350° C., the reaction pressure is controlled to preferably 0.01 mmHg to 100 kg/cm$^2$, more preferably 10 mmHg to 10 kg/cm$^2$ The reaction time of the second stage (A-b), which refers to a residence time of the reaction product mixture fed from the first stage (A-a) to the second stage (A-b) in the second reactive distillation column, is variable depending on the reaction conditions and type It and operation conditions of the second column. Usually, when the reaction temperature in the second stage (A-b) is 50° to 350° C., the reaction time is preferably 0.001 to 50 hours, more preferably 0.001 to 10 hours.

The liquid phase fraction delivered from the second reactive distillation column A2 is fed into a separator B of the stage (B), to collect the diaryl oxalate, a liquid phase fraction delivered from the separator B is fed into a reactor C of the decarbonylation step (C), to decarbonylate the diaryl oxalate to convert it diaryl carbonate, and a liquid phase fraction delivered from the reactor C is fed into a refining apparatus D for the collection step (D) to refine and collect the diaryl carbonate.

In the step (C) of the process of the present invention, the diaryl oxalate contained in the liquid phase fraction delivered from the step (B) is decarbonylated preferably in the presence of a decarbonylation catalyst, to convert it to a diaryl carbonate and carbon monoxide.

The decarbonylation catalyst usable for the step (C) of the process of the present invention is preferably capable of decarbonylating the diaryl oxalate at a relatively low temperature of about 100° C. to about 350° C. at a high selectively of preferably at least 50 molar %, more preferably 60 to 100 molar %, to provide a diaryl carbonate.

The decarbonylation catalyst preferably comprises at least one phosphorus compound having at least one carbonphosphorus bond. This type of phosphorus compound is preferably selected from organic phosphine compound of the general formula (w), organic phosphine oxide compounds of the general formula (x), organic phosphine dihalide compounds of the general formula (y) and organic phosphonium salt compounds of the general formula (z).

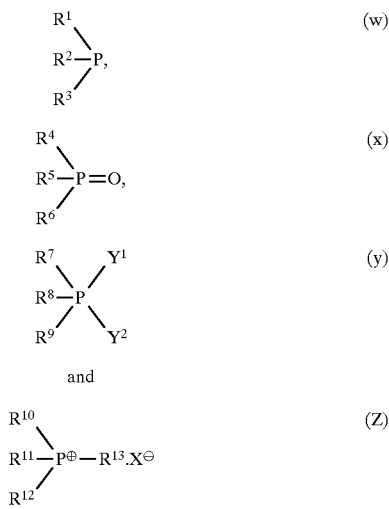

In the above general formulae (w), (x), (y) and (z), $R^1$ to $R^{13}$ represent respectively and independently from each other a member selected from the group consisting of a hydrogen atom, alkyl groups having 1 to 16 carbon atoms, aryl groups having 6 to 16 carbon atoms, substituted aryl groups, aralkyl group having 7 to 22 carbon atoms, and substituted aralkyl groups provided that at least one of $R^1$, $R^2$ and $R^3$, at least one of $R^4$, $R^5$ and $R^6$, at least one of $R^7$, $R^8$ and $R^9$ and at least one of $R^{10}$, $R^{11}$, and $R^{12}$ and $R^{13}$ are not a hydrogen atom, X represent an anionic atom or atomic group, and $Y^1$ and $Y^2$ represent respectively and independently from each other a halogen atom.

The substituted aryl groups have at least one substituent directly attached to a carbon atom located in the aryl ring structure. Also, the substituted aralkyl groups have at least one alkyl moiety and at least one substituent other than the alkyl group, and directly attached to a carbon atom located in the aryl ring structure.

The substituent for the substituted aryl groups and the substituted aralkyl groups is preferably selected from the group consisting of halogen atoms, for example, fluoride chlorine and bromide atoms, a nitro group, alkyl groups having 1 to 16 carbon atoms, and alkoxyl group having 1 to 16 carbon atoms.

Two of $R^1$ to $R^3$, two of $R^4$ to $R^6$, two of $R^7$ to $R^9$ and two of $R^{10}$ to $R^{13}$ may be connected or cross-linked to each other.

In the phosphorus compounds of the formulae (w) to (z), the alkyl groups represented by $R^1$ to $R^{13}$ and having 1 to 16 carbon atoms include methyl, ethyl, n-propyl, isopropyl, n-butyl, isobutyl, n-pentyl, n-hexyl, n-heptyl, and n-octyl groups, the aryl groups represented by $R^1$ to $R^{13}$ and having 6 to 16 carbon atoms include phenyl and naphthyl, the substituted aryl groups represented by $R^1$ to $R^{13}$ include methylphenyl, ethylphenyl, propylphenyl, methoxyphenyl, ethoxyphenyl, propoxyphenyl, chlorophenyl, fluorophenyl, methylnaphthyl, methoxynaphthyl, nitronaphthyl and chloronaphthyl groups, and the aralkyl groups represented $R^1$ to $R^{13}$ and having 7 to 22 carbon atoms include benzyl, phenethyl, p-methylbenzyl, p-methoxybenzyl and p-methylphenethyl.

In the phosphine compounds of the formula (w), preferably all of $R^1$ to $R^3$ are the aryl or substituted aryl groups as defined above. However, in the phosphine compounds, one or two, preferably two, of $R^1$ to $R^3$ may be the aryl or substituted aryl groups and the remaining (s) may be an alkyl, aralkyl or substituted aralkyl group.

The phosphine compounds of the formula (w) in which all of $R^1$ to $R^3$ are the aryl or substituted aryl groups are preferably selected from triphenylphosphine, tris (4-chlorophenyl) phosphine, tris (4-tolyl) phosphine, and α-naphthyl-(phenyl)-4-methoxyphenylphosphine.

The phosphine compounds of the formula (w) in which one or two of $R^1$ to $R^3$ are the aryl or substituted aryl groups and the remailing(s) is an alkyl, aralkyl or substituted aralkyl group, are selected from, for example, methyldiphenylphosphine, phenyl(p-methoxyphenyl) methylphosphine ethyl(phenyl)-n-propylphosphine and dimethylphenylphosphine.

In the phosphine oxide compounds of the formula (x), all of $R^4$ to $R^6$ are preferably the aryl or substituted aryl groups. However, one or two of $R^4$ to $R^6$ may be the aryl or substituted aryl groups and the other two or one may the alkyl, aralkyl or substituted aralkyl group.

The phosphine oxide compounds of the formula (x) in which all of $R^4$ to $R^6$ are the aryl or substituted aryl groups, are preferably selected from triphenylphosphine oxide, tris (4-chlorophenyl) phosphine oxide, tris (4-tolyl) phosphine oxide and a-naphthyl(phenyl)-4-methyoxyphenylphosphine oxide.

The phosphine oxide compounds of the formula (x), having one or two aryl or substituted aryl groups and two or one alkyl, aralkyl or substituted aralkyl group are preferably selected from methyldiphenylphosphine oxide, phenyl(p-methoxyphenyl)-methylphospline oxide, ethyl(phenyl)-n-propylphosphine oxide, ethyl(phenyl)-n-propylphosphine oxide and dimethylphenylphosphine oxide.

Among the phosphine dihalide compounds of the formula (y), it is preferable that all of $R^7$ to $R^9$ are the aryl or substituted aryl groups. However, one or two of $R^7$ and $R^9$ may be the aryl or substituted aryl groups and the other two or one of $R^7$ to $R^9$ may be the alkyl, aralkyl or substituted aralkyl group.

Also, in the formula (y), $Y^1$ and $Y^2$ may be the same as or different from each other and represent respectively a chlorine, bromine or iodine atom.

The phosphine dihalide compounds of the formula (y) in which all of $R^7$ to $R^9$ are the aryl or substituted aryl groups as defined above are preferably selected from triphenylphosphine dichloside, triphenylphosphine bromide, triphenylphosphine iodide.

In the phosphonium compounds of the formula (z), it is preferable that all of $R^{10}$ to $R^{13}$ are the aryl or substituted aryl groups, and $X^{31}$ is selected from halogen ions, aliphatic carboxylate ions and fluoroborate ion. However, in the formula (z), one to three, especially two or three of $R^{10}$ to $R^{13}$ may be the aryl and substituted aryl groups and the other one to three, especially one or two, of $R^1$ to $R^{13}$ may be the alkyl, aralkyl or substituted aralkyl groups, and X may be selected from halogen ions, aliphatic carboxylate ions and a fluoroborate ion.

The phosphonium compounds of the formula (z) wherein all of $R^{10}$ to $R^{13}$ are the aryl or substituted aryl groups mentioned above, and $X^e$ is selected from halogen ions are preferably selected from tetraphenylphosphonium chloride tetraphenylphosphonium bromide, tetraphenylphosphonium iodide, 4-chlorophenyltriphenylphosphonium chloride, 4-chlorophenyltriphenylphosphonium bromide 4-chlorophenyltriphenylphosphonium iodide, 4-ethoxyphenyltriphenylphosphonium chloride, 4-ethoxyphenyltriphenylphosphonium bromide, 4-ethoxyphenyltriphenylphosphonium iodide, 4-methylphenyltriphenylphosphonium chloride, 4-methylphenyltriphenylphosphonium bromide, 4-methylphenyltriphenylphosphonium iodide, 9-fluorenylphenyltriphenylphosphonium chloride, and 9-fluorenylphenyltriphenylphosphonium bromide.

The phosphonium compounds of the formula (z) wherein all of $R^{10}$ to $R^{13}$ are the aryl or substituted aryl groups mentioned above, and $X^e$ is selected from aliphatic carboxylate ions are preferably selected from tetraphenylphosphonium acetate, 4-chlorophenyltriphenylphosphonium acetate, 4-ethoxyphenyltriphenylphosphonium acetate and 4-methylphenyltriphenylphosphonium acetate.

The phosphonium compounds of the formula (z) wherein all of $R^{10}$ to $R^{13}$ are the aryl or substituted aryl groups mentioned above, and $X^e$ is a fluoroborate are preferably selected from tetraphenylphosphonism fluoroborate, 4-chlorophenyltriphenylphosphonium fluoroborate, 4-ethoxyphenyltriphenylphosphonium fluoroborate and 4-methylphenyltriphenylphosphonium fluoroborate.

Some of the phosphonium compounds of the formula (z) which are commercially available can be produced by known synthesis methods as, for example, disclosed in Bull. Chem. Soc. Jpn., 56, 2869(1989) and J. Am. Chem. Soc., 70, 737, (1948).

For example, a tetraarylphosphonium chloride can be prepared by reacting a triarylphosphine with a corresponding aryl iodide or bromide in the presence of a catalyst consisting of palladium acetate, and converting the resultant tetraarylphosphonium iodide or bromide to a corresponding tetraarylphosphonium chloride by using an ion-exchange resin (chlorine type). Alternatively, the tetraarylphorphonium salts having an anion other than halogen ions can be prepared by reacting a corresponding tetraarylphosphonium chloride with an alkali metal salt (for example, sodium or potassium salt) or an ammonium salt of an organic or inorganic acid, for example, an aliphatic carboxylic acid or fluoroboric acid.

The phosphonium salt compound other than the tetraarylphosphonium salts can be prepared by the analogous methods to those mentioned above.

In the step (C) of the process of the present invention, the decarbonylation catalyst may consists of one or more of the above-mentioned organic phosphorus compounds. Also, the decarbonylation catalyst may be dissolved or suspended in the reaction mixture fed into the step (C).

In the step (C), the decarbonylation catalyst is preferably employed in an amount of 0.001 to 50 molar %, more preferably 0.01 to 20 molar %, based on the molar amount of the diaryl oxalate supplied to the step (C).

The decarbonylation catalyst for the step (c) containing at least one organic phosphorus-containing compound may be used together with a promoter comprising at least one member selected from inorganic halogen compounds and organic halogen compounds. Usually, the promoter is used preferably in an amount of 0.01 to 150 times, more preferably 0.1 to 100 times, the total molar amount of the-organic phosphorus compound in the catalyst.

The inorganic halogen compounds usable as a promoter are selected from preferably, halogenated aluminum compounds, for example, aluminum chloride and aluminum bromide; halogenated platinum group metal compounds, for example, platinum chloride, chloroplatinic acid, ruthenium chloride, and palladium chloride; halogenated phosphorus compounds, for example, phosphors trichloride, phosphorus pentachloride, phosphorus oxychloride, phosphorus tribromide, phosphorus pentabromide and phosphors oxybromide; hydrogen halides, for example, hydrogen chloride and hydrogen bromide; halogenated sulfur compounds, for example, thionyl chloride, sulfuryl chloride, sulfur dichloride and disulfur dichloride; and halogens, for example, chlorine and bromine. Among the inorganic halogen compounds mentioned above, inorganic chlorinated compounds and inorganic brominated compounds are preferably employed, and the inorganic chlorinated compounds are more preferably employed for the present invention.

The organic halogen compounds usable as the promoter are preferably selected from organic compounds having at least one atom selected from carbon, hydrogen, oxygen, nitrogen, sulfur and silicon and at least one halogen atom (for example, chlorine or bromine atom).

The organic halogen compounds may have at least one structure selected from structures in which at least one halogen atom is bounded to a saturated carbon atom, structures in which a halogen atom is bonded to a carbonyl carbon atom, structures in which at least one halogen atom is bonded to a silicon atom, and structures in which a halogen atom is bonded to a sulfur atom.

The organic halogen compounds having at least one structure in which at least one halogen atom is bonded to a saturated carbon atom are preferably selected from halogenated alkyl compounds, for example, chloroform, carbon tetrachloride, 1,2-dichloroethane, butyl chloride, and dodecyl chloride; halogenated aralkyl compounds, for example, benzyl chloride, benzo-trichloride, triphenylmethyl chloride, and α-bromo-o-xylene; halogen-substituted aliphatic nitrile compounds, for example, β-chloropropionitrile and γ-chlorobutyronitrile; and halogen-substituted aliphatic carboxylic acids, for example, chloroacetic acid, bromoacetic acid and chloropropionic acid).

The organic halogen compounds having at least one structure in which a halogen atom is bonded to a carbonyl carbon atom include acid halide compounds, for example, acetyl chloride, oxalyl chloride, propionyl chloride, stearoyl chloride, benzoyl chloride, 2-naphthalene carboxylic acid chloride, and 2-thiophenecarboxylic acid chloride; and aryl haloformate ester, for example, phenyl chloroformate.

The organic halogen compounds having at least one structure in which at least one halogen atom is bonded to a silicon atom include halogenated silane compounds, for example, diphenyl dichlorosilane and triphenylchlorosilane.

The organic halogen compounds having at least one structure in which a halogen atom is bonded to a sulfur atom, include sulfonyl chlorides, for example, p-toluenesulfonic acid chloride and 2-naphthalenesulfonic acid chloride.

In the decarbonylation step (C) of the process of the present invention, the type of the decarbonylation reaction is not limited to a specific reaction. Preferably, the decarbonylation reaction of the diaryl oxalate ester in the step (C) is carried out in the presence of a specific decarbonylation catalyst comprising at least one phosphorus containing organic compound. In this case, the liquid phase fraction supplied from the step (B) and containing the diaryl oxalate is fed together with the decarbonylation catalyst into a decarbonylation reactor C and subjected to the decarbonylation reaction at a temperature of, preferably 100° to 450° C., more preferably 160° to 400° C., still more preferably 180° to 350° C., while removing the resultant by product comprising carbon monoxide gas. There is no limitation to the reaction pressure for the step (C). Usually, the decarbonylation reaction can be carried out under a pressure of 100 mmHg to 10 kg.cm².

Preferably, the decarbonylation reaction is carried out in liquid phase and, usually, no reaction medium is necessary. Optionally, a protonic solvent, for example, N-methylpyrrolidone or sulfolane, is used as a reaction medium for the decarbonylation reaction.

The reactor for the decarbonylation step (C) is not limited to a specific type of reactor as long as the reactor enables the diaryl oxalate to be decarbonylated into a corresponding diaryl carbonate and carbon monoxide. Also, there is no limitation to the type of materials for the reaction apparatus for the step (C). Usually the reactor for the step (C) is made mainly from a glass, stainless steel (SUS), an aluminum alloy or a nickel alloy.

The reactor for the step (C) may be selected from full-mixing type (or agitation type) reactors with single or multiple reaction vessels and cylinder type or column type reactors with a multi-pipe type heat exchanger. The cylinder or column type reactor is optionally provided with one or more filler packed portions or one or more baffles for enhancing the mixing effect. Also, the reactor may have a wetting wall.

A liquid phase fraction delivered from the reactor of the step (C) contains non-reacted diaryl oxalate and the decarbonylation catalyst in addition to the target diaryl carbonate. The collection of the diaryl carbonate from the liquid phase fraction can be carried out by the step (D) using a conventional refining-collecting apparatus.

The refining and collecting apparatus for the step (D) may be carried out by separating and recovering the decarbonylation catalyst by means of an evaporator or thin membrane evaporator, and by subjecting the resultant vapor phase fraction to a distiller having a certain number of filler-packed layers or trays, to collect the target diaryl carbonate with a high degree of purity.

As mention above, a diaryl oxalate can be produced by a process of the present invention comprising the steps of:
  (1) subjecting a dialkyl oxalate and a phenol compound to a first transesterification reaction in the presence of a transesterification catalyst in a first reactive distillation column, while evaporating away a reaction by-product comprising a corresponding alkyl alcohol from the first column;
  (2) subjecting the reaction product mixture delivered from the first column to a second transesterification reaction in a second reactive distillation column, while evaporating away a reaction by-product comprising a corresponding dialkyl oxalate; and
  (3) distilling the reaction product mixture delivered from the second column to collect the resultant diaryl oxalate.

Namely, in the process of the present invention, the step (A) is carried out in two stages consisting of a first stage (A-a) in which a dialkyl oxalate and a phenol compound are subjected to a first transesterification reaction in the presence of a transesterification catalyst in a first reactive distillation column, while evaporating away a resultant reaction by-product comprising a corresponding alkyl alcohol from the first column; and a second stage (A-b) in which the resultant reaction product mixture delivered from the first column and containing the transesterification catalyst is subjected to a second transesterification reaction in a second reactive distillation column, while evaporating away a resultant reaction by-product comprising a corresponding dialkyl oxalate from the second column, and the step (B) is carried out by distilling the reaction product mixture delivered from the second column, to collect the resultant diaryl oxalate.

In an embodiment of the diaryl oxalate-producing procedures, the first stage (A-a) and the second stage (A-b) of the step (A) and the step (B) are carried out as follows.

In the first stage (A-a) of the step (A), a dialkyl oxalate a phenol compound and a transesterification catalyst are fed into the first reactive distillation column, and the transesterification reaction of the dialkyl oxalate with the phenol compound in the presence of the transesterification catalyst is carried out, while withdrawing a resultant first vapor phase fraction containing a corresponding alkyl alcohol from the top portion of first column; in the second stage (A-b) of the step (A), a resultant liquid phase fraction of the first stage (A-a) containing an alkylaryl oxalate is fed from the bottom portion of the first column into the second reactive distillation column through a conduit, and subjected to the second transesterification reaction to allow the alkylaryl oxalate contained in the liquid phase fraction to be transesterified into corresponding diaryl oxalate and dialkyl oxalate, while withdrawing a resultant second vapor phase fraction containing the dialkyl oxalate from the top portion of the second column; and in the step (B), a resultant liquid phase fraction of the second stage (A-b) containing the diaryl oxalate is fed, from the bottom portion of the second column into a distillation column and distilled therein, and a resultant third vapor phase fraction comprising the distilled diaryl oxalate is withdrawing and collected from the distillation column.

Figure 6:
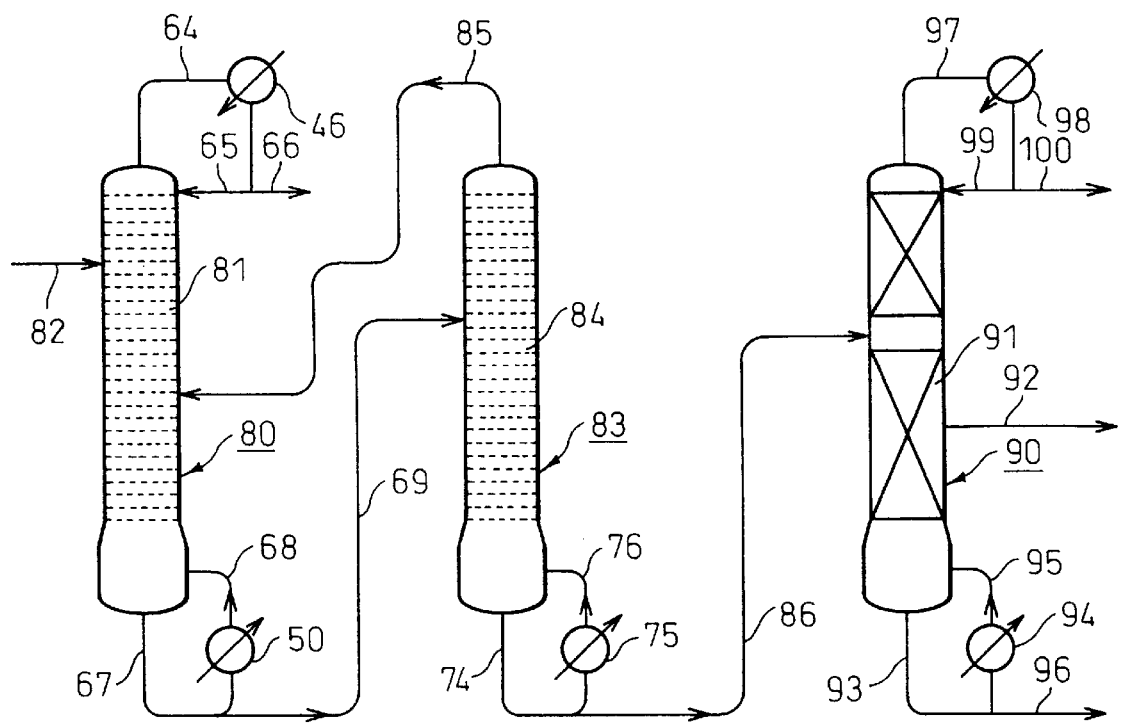
FIG. 6 is an explanatory cross-sectional view of an embodiment of the apparatus for carrying out the steps (A) and (B) of the process of the present invention.

In FIG. 6 showing the above-mentioned embodiment of the steps (A) and (B) of the present invention, a reaction mixture of a dialkyl oxalate, a phenol compound and a transesterification catalyst are fed into a first reactive distillation column 80 having a plurality of reactive distillation trays or filler-packed layers 81 through a conduit 82, and subjected to the same first transesterification reaction as in FIG. 5, while withdrawing the resultant first vapor phase fraction containing an alkyl alcohol from the top portion of the first column 80 through the conduit 64. The resultant first liquid phase fraction containing the alkylaryl oxalate and the catalyst is withdrawn from the bottom portion of the first column 80 through a conduit 67 and fed into a second reactive distillation column 83 having a plurality of reactive distillation trays or filler-packed layers 84 through a conduit 69. In the second column 83, the alkylaryl oxalate contained in the liquid phase fraction is transesterified (disproportionated) into a diaryl oxalate and a dialkyl oxalate.

A resultant second vapor phase fraction containing the dialkyl oxalate is withdrawn from the top portion of the second column 83 and fed into a middle portion of the first column 80 through a conduit 85.

Also, a resultant second liquid phase fraction containing the diaryl oxalate and the catalyst is withdrawn from the bottom portion of the second column 83 through a conduit 74 and fed into a distiller 90 for the step (B) through a conduit 86, to collect the diaryl oxalate from the liquid phase fraction.

The distiller 90 is preferably a continuous or multi-step distiller which is optionally provided with a refining distiller (not shown in FIG. 6). The distiller 90 preferably has a theoretical plate number of 5 or more (filler-packed layers or distillation trays 91).

The second liquid phase fraction is distilled in the distiller 90 to concentrate the diaryl oxalate, and a resultant third vapor phase fraction containing the concentrated diaryl oxalate is withdrawn preferably from the middle portion of the distiller 90 through a conduit 92. A portion of the liquid phase fraction reached the bottom portion in the distiller 90 is circulated through a conduit 93, a heater 94 and a conduit 95 to control the temperature of the liquid phase fraction to a desired level, and a portion of the liquid phase fraction containing the catalyst and high boiling temperature substances is withdrawn from the distiller 90 through a conduit 96. Preferably, a portion of a vapor phase fraction reached the top portion of the distiller 90 and containing light ends such as alkylaryl oxalate is withdrawn from the top portion of the distiller 90 through a conduit 97, and cool-condensed by a cooler 98. A portion of the condensed liquid is recycled to the top portion of the distiller 90 preferably at a reflux ratio of 0 to 20, more preferably 0 to 10, through a conduit 99, and the remaining potion of the condensed liquid is discharged to the outside of the collection system of the step (B) through a conduit 100. The liquid phase fraction delivered from the collection system of the step (B) is optionally recycled to the first and/or second column to re-utilize the catalyst. Optionally, the catalyst is recovered from the delivered liquid phase fraction of the distiller 90 and is reactivated, and the reactivated catalyst is reused for the step (A) of the present invention.

In the distillation procedure in the distiller 90, the temperature of the liquid fraction is controlled to a desired level of, preferably 50° to 350° C., more preferably 140° to 280° C., still more preferably 180° to 250° C., so as to minimize the thermal deterioration of the reactants.

The distillation in the step (B) can be carried out under a reduced pressure, the ambient atmospheric pressure or an increased pressure. Preferably, the distillation pressure is adjusted to a level at which the vapor phase fraction containing the concentrated diaryl oxalate can be collected at the middle portion of the distiller while minimizing the thermal deterioration of the diaryl oxalate. Therefore, usually the distillation pressure is preferably 0.1 mmHg to 5 kg/cm more preferably 1 mmHg to 1 kg/cm$^2$.

The third vapor phase fraction withdrawn from the middle portion of the distiller 90 and containing the concentrated diaryl oxalate is optionally cool-condensed and the condensed liquid is recovered and is supplied to the next step. If necessary, the condensed liquid is further refined by washing with water and/or by a refining distillation using a refining distillation column, to eliminate impurities therefrom.

In another embodiment of the steps (A) and (B) of the process of the present invention, the following procedures are carried out.

In the first stage (A-a) of the step (A) a dialkyl oxalate, a phenol compound and transesterification catalyst are fed into the first reactive distillation column, and transesterification reaction of the dialkyl oxalate with the phenol compound in the presence of the transesterification catalyst is carried out, while withdrawing a resultant first vapor phase fraction containing a corresponding alkyl alcohol from the top portion of the first column; in the second stage (A-b) of the step (A), a resultant liquid phase fraction of the stage (A-a) containing an alkylaryl oxalate is fed from the bottom portion of first column into the second reactive distillation column, and is subjected to the second transesterification reaction to allow the alkylaryl oxalate contained in the liquid phase fraction to be transesterified into corresponding diaryl oxalate and dialkyl oxalate, while withdrawing a resultant second vapor phase fraction containing the dialkyl oxalate from the top portion of the second column; and in the step (B), a resultant liquid phase fraction of the stage (A-b) containing the diaryl oxalate is fed from the bottom portion of the second column into an evaporator and is evaporated therein, a resultant vapor has fraction generated in the evaporator is fed from the evaporator into a first distiller and is distilled therein, while withdrawing a vapor phase fraction generated in the first distiller and containing the alkylaryl oxalate from the top portion of the first distiller, a resultant liquid phase fraction generated in the first distiller and containing the diaryl oxalate is fed from the bottom portion of the first distiller into a second distiller and is distilled therein, and a resultant third vapor phase fraction containing the diaryl oxalate is withdrawn and collected from the second distiller.

Figure 7:
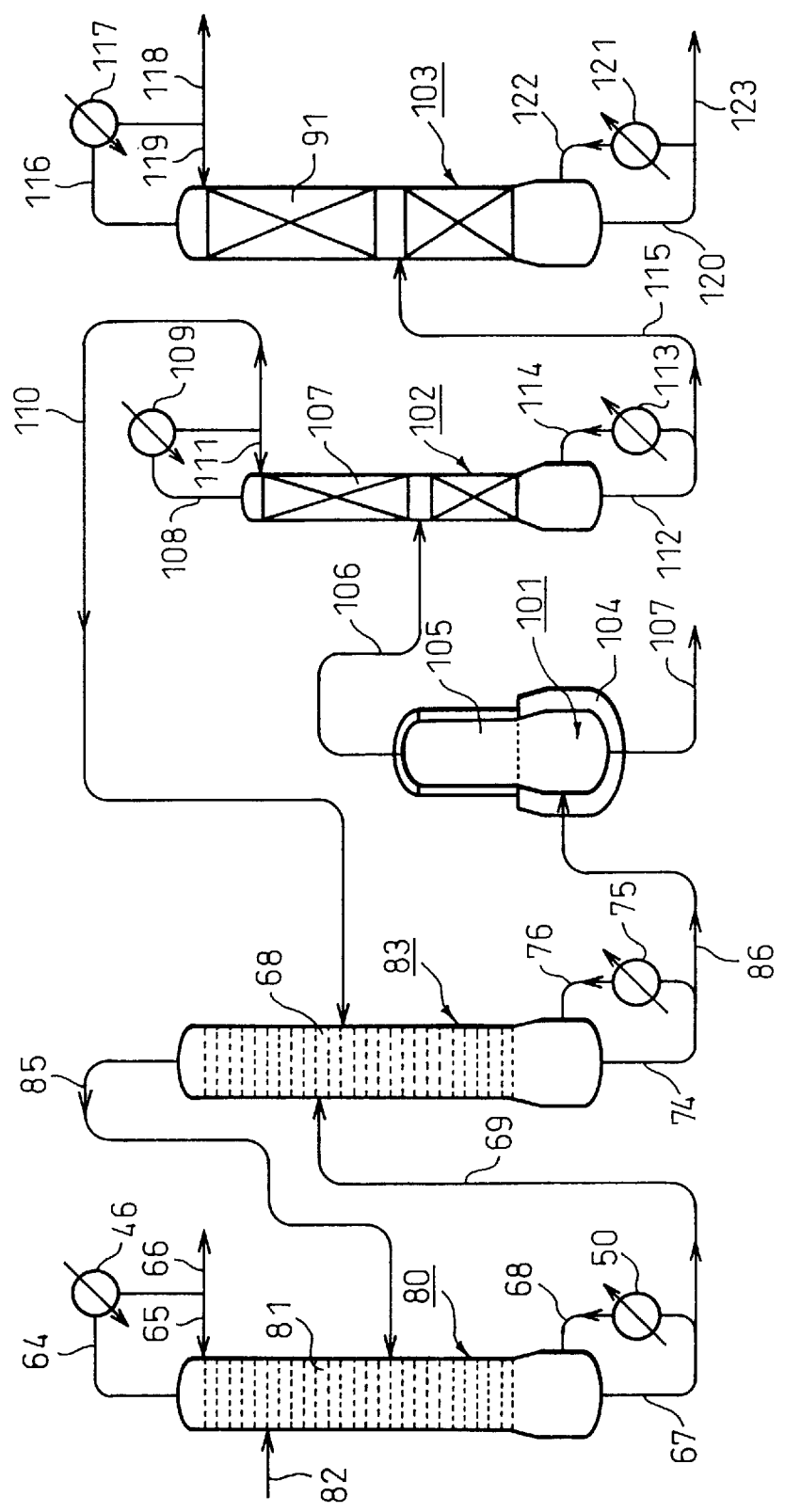
FIG. 7 is an explanatory cross-sectional view of another embodiment of the apparatus for carrying out the steps (A) and (B) of the process of the present invention.

Referring to FIG. 7, the step (A) is carried out in the first stage (A-a) and the second stage (A-b) using the first and second reactive distillation column 80 and 83 in the same manner as in FIG. 6, and a portion of the second liquid phase fraction delivered from the bottom portion of the second column 83 and containing the diaryl oxalate and the catalyst is fed into a collection system for the step (B) including an evaporator 101, a first distiller 102 and a second distiller 103.

In FIG. 7, the second liquid phase fraction is fed into a bottom portion of the evaporator 101. The bottom portion is provided with a heating jacket 104 to heating the liquid phase fraction at an evaporating temperature thereof, and is connected to a top portion 105 for containing the resultant vapor. In the bottom portion 104, the liquid phase fraction is heated to generate a vapor containing the diaryl oxalate and small amounts of starting and intermediate compounds. The resultant vapor phase fraction is withdrawn from the top portion 105 of the evaporator 101 and fed into a middle portion of the first distiller 102 through a conduit 106. Also, the remaining liquid phase fraction containing the catalyst and heavy ends is withdrawn from the bottom portion 104 of the evaporater 101 through a conduit 107.

The first distiller 102 preferably has a theoretical plate number of 5 or more (distillation trays or filler-packed layers 107), and the fed liquid phase fraction is distilled to separate a liquid phase fraction containing concentrated diaryl oxalate from a vapor phase fraction containing substances having lower boiling temperatures than that of the diaryl oxalate at the distillation pressure.

The resultant vapor phase fraction of the first distiller 102 containing, mainly the alkylaryl oxalate and non-reacted phenol is withdrawn from the top portion of the first distiller 102 through a conduit 108 and cool-condensed by a cooler 109. Optionally, a portion of the condensed liquid is recycled into the middle portion of the second reactive distillation column 83 for the stage (A-b) through a conduit 110, and the remaining portion of the condensed liquid is recycled into the top portion of the first distiller 102 through a conduit 111. Alternatively, the cool-condensing procedure by the cooler 109 for the vapor phase fraction is omitted.

The resultant liquid phase fraction containing the concentrated diaryl oxalate is withdrawn from the bottom portion of the first distiller 102 through a conduit 112. A portion of the withdrawn liquid phase fraction is heated to a desired temperature by a heater 113 and recycled into the bottom portion of the first distiller 102 through a conduit 114. The recycling of the heated portion of the liquid phase fraction is contributory to maintaining the distillation temperature of the first distiller 102 at a desired level of preferably 50° to 300° C., more preferably 80° to 250° C., still more preferably 100° to 230° C. The first distillation procedure in the first distiller 102 can be carried out under a reduced pressure, the ambient atmospheric pressure or an increased pressure, as long as the fraction containing the alkylaryl oxalate can be evaporated and delivered from the top portion of the first distiller. Usually, the first distillation pressure is preferably 0.1 mmHg to 2 kg/cm$^2$, more preferably 1 mmHg to 1 kg/cm$^2$. The remaining portion of the withdrawn liquid phase fraction is fed into a middle portion of the conduit 115.

The second distiller 103 has the same structure as in the distiller 90 in FIG. 6 and is operated under the same conditions as in the distiller 90 in FIG. 6, to refine the diaryl oxalate. In the second distiller 103, the resultant vapor phase fraction containing the refined diaryl oxalate in a high concentration of 95% by weight or more is withdrawn from the top portion of the second distiller 103 through a conduit 116, and cool-condensed by a cooler 117. The condensed liquid containing the refined diaryl oxalate is collected through a conduit 118. Optionally, a portion of the condensed liquid is recycled into the top portion of the second distiller 103 through a conduit 119.

Also, a resultant liquid phase fraction is withdrawn from the bottom portion of the second distiller 103. Optionally, a portion of the withdrawn liquid phase fraction is heated by a heater 121 and recycled into the bottom portion of the second distiller 103 through a conduit 122 and the remaining portion of the liquid phase fraction is discharged from the collection system through a conduit 123. The recycling of the heated portion of the liquid phase fraction is contributory to maintaining the second distillation temperature of the second distiller 103 at a desired level.

The condensed liquid recovered from the cooler 117 of the second distiller 103 contains the diaryl oxalate in a high concentration of at least about 95% by weight, usually 98% by weight or more. If necessary, the degree of purity of the diaryl oxalate in the condensed liquid can be increased to 99.0% by weight or more, particularly 99.5% by weight or more, by washing the condensed liquid with water, or by applying a refining distillation thereto in a refining distillation column, to remove impurities therefrom.

In still another embodiment of the steps (A) and (B) of the process of the present invention, the following procedures are carried out.

In first stage (A-a) of the step (A), a dialkyl oxalate, a phenol compound and a transesterification catalyst are fed into the first reactive distillation column, and the transesterification reaction of the dialkyl oxalate with the phenol compound in the presence of the transesterification catalyst is carried out, while withdrawing a resultant first vapor phase fraction containing a corresponding alkyl alcohol from the top portion of the first column; in the second stage (A-b) of the step (A), a resultant liquid fraction of the stage (A-a) containing an alkylaryl oxalate is fed from the bottom portion of the first column into a second reactive distillation column, and is subjected to the second transesterification reaction to allow the alkylaryl oxalate contained in the liquid phase fraction to be transesterified into corresponding diaryl oxalate and dialkyl oxalate, while withdrawing a resultant second vapor fraction of the second stage (A-b) containing the dialkyl oxalate from the top portion of the second column; and in the step (B), a resultant liquid fraction of the second stage (A-b) containing the diaryl oxalate is fed from the bottom portion of the second column into a first distiller and is distilled therein, while withdrawing a resultant vapor phase fraction containing the alkylaryl oxalate from the top portion of the first distiller, a resultant liquid fraction generated in the first distiller and containing the diaryl oxalate is fed from the bottom portion of the first distiller into a second distiller and is distilled therein, and a resultant third vapor phase fraction generated in the second distiller and containing the diaryl oxalate is withdrawn and collected from the second distiller.

Figure 8:
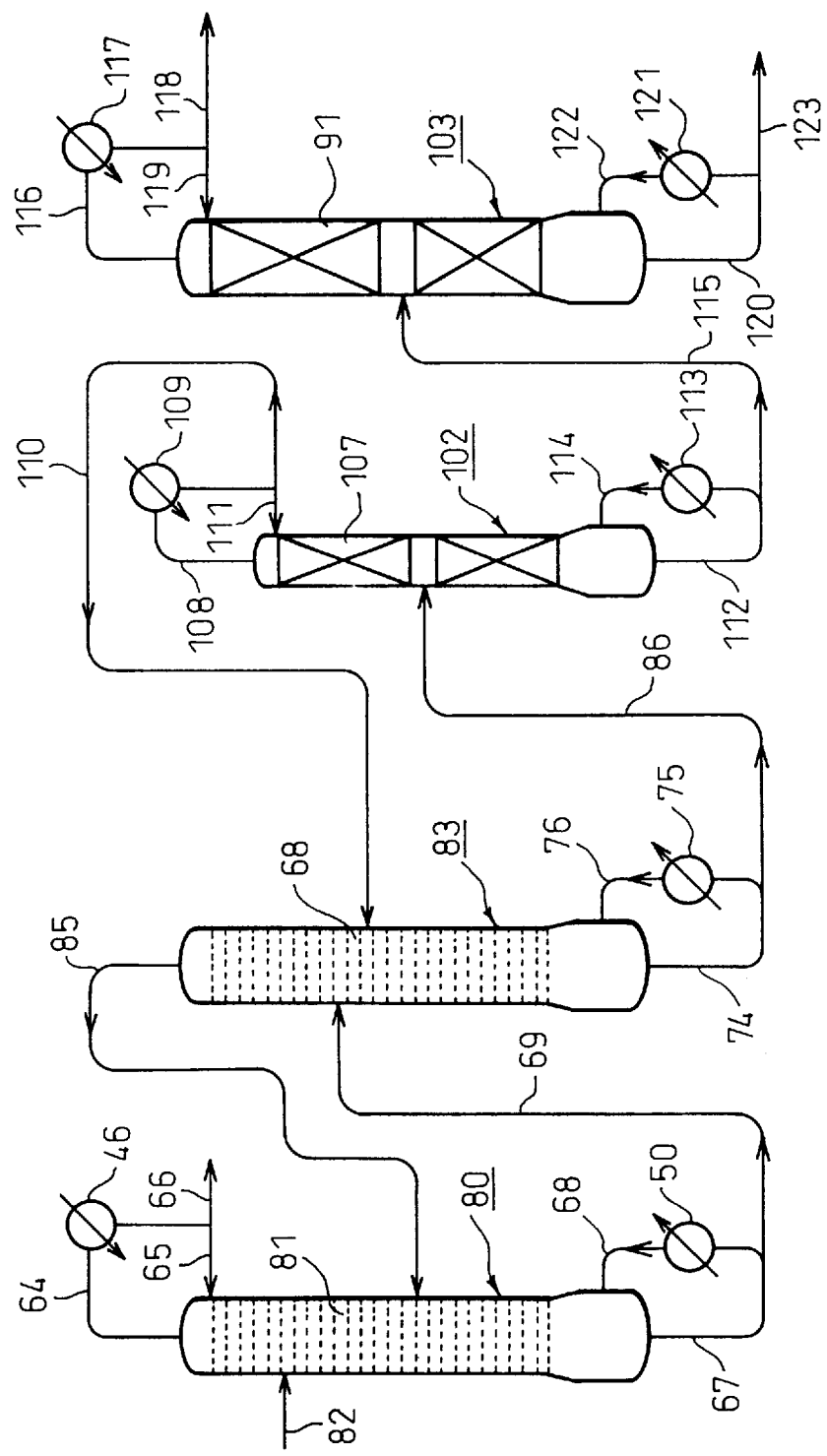
FIG. 8 is an explanatory cross-sectional view of still another embodiment of the apparatus for carrying out the steps (A) and (B) of the process of the present invention.

The above, mentioned procedures for the steps (A) and (B) can be carried out by using the apparatus as shown in FIG. 8.

In FIG. 8, the step (A) consisting of the same stages (A-a) and (A-b) using the same reactive distillation columns 80 and 83 as in FIG. 7 is carried out under the same conditions as in FIG. 7.

The resultant liquid phase fraction delivered from the bottom portion of the second reactive distillation column 83 is directly fed into the middle portion of the first distiller 102 through the conduit 86. Namely, in the collection apparatus of FIG. 8, the evaporator 101 of FIG. 7 is omitted.

In FIG. 8, the liquid phase fraction delivered from the second reactive distillation column 83 is distilled in the first distiller 102, and then the liquid phase fraction delivered from the bottom portion of the first distiller 102 is refined in the second distiller 103, under the similar conditions as in FIG. 7. The final liquid phase fraction containing the diaryl oxalate in a high concentration can be collected from the bottom portion of the second distiller 103.

EXAMPLES

The present invention will be further explained by the following examples.

Example 1 (Stage (A-a) of step (A))

As a first reactive distillation column, a fifty plate number Oldershaw type distiller having an inner diameter of 32 mm and provided with a one liter bottom flask was used.

A solution consisting of 61.2% by weight of phenol, 38.5% by weight of dimethyl oxalate and 0.3% by weight of tetraphenoxytitanium was fed into the twelfth step from the top of the first reactive distillation column at a flow rate of 300 ml/hr. The bottom flask was heated by a mantle heater at a temperature of 190° C., to promote the first transesterification reaction of dimethyl oxalate with phenol. The resultant vapor phase fraction was continuously withdrawn from the top portion of the column and condensed by a cooler, while maintaining the amount of the liquid phase fraction contained in the bottom flask at a level of 500 ml. A portion of the condensed liquid was recycled at a reflux ratio of 2 and the remaining portion of the condensed liquid was delivered.

When the reaction in the first column was stabilized in temperature and composition of the liquid phase fraction, namely 5 hours after the start of the feeding of the reaction material mixture, the liquid phase fraction in the bottom flask was analyzed by gas chromatography. It was found that the liquid phase fraction of the first column consisted of 23.45% by weight of dimethyl oxalate, 26.76% by weight of methylphenyl oxalate, 6.74% by weight of diphenyl oxalate and 42.62% by weight of phenol. The withdrawal rate of the liquid phase fraction from the bottom flask of the first column was about 306 g/hr. The vapor phase fraction consisted of 99.7% by weight of methyl alcohol and 0.3% by weight of dimethyl oxalate and it was withdrawn in the state of a condensed liquid, at a flow rate of about 24 g/hr from the first column.

Example 2 (Stage (A-b) of step (A))

As a second reactive distillation column, the same Oldershaw type distiller as in Example 1 was used.

The liquid phase fraction withdrawn from the first column of Example 1 was fed into the twelfth step from the top of the second column at a flow rate of 300 ml/hr, while heating the bottom flask of the second column at a temperature of 230° C., to subject the reactants in the fed liquid phase fraction to a second transesterification (disproportionation) reaction. The resultant gas phase fraction was withdrawn from the top position of the second column and condensed by a cooler, and the resultant condensed liquid was delivered without recycling it into the second column. The amount of the resultant liquid phase fraction in the bottom flask was maintained at a level of 500 ml. When the reaction conditions in the second column was stabilized in temperature and composition of the liquid phase fraction, namely 5 hours after the start of feeding, the liquid phase fraction in the bottom flask was analyzed by gas-chromatography. It was found that the liquid phase fraction consisted of 2.82% by weight of dimethyl oxalate, 27.81% by weight of methylphenyl oxalate, 54.74% by weight of diphenyl oxalate, and 13.64% by weight of phenol. The liquid phase fraction was withdrawn at a rate of about 126 g/hr from the bottom portion of the second column.

The condensed liquid of the gas phase fraction consisted of 2.32% by weight of methyl alcohol, 45.23% by weight of dimethyl oxalate, 46.95% by weight of phenol, 5.37% by weight of methylphenyl oxalate and 0.13% by weight of diphenyl oxalate and was withdrawn at a rate of about 189 g/hr.

Example 3 (Collection step (B))

A first glass distiller packed with Helipack packings (5(D)×5(H) mm) and having an inner diameter of 20 mm and a length of 2 m was used.

The liquid phase fraction withdrawn from the second reactive distillation column of Example 2 was fed into the first distiller through an inlet located 80 cm below the top of the distiller at a feeding rate of 100 ml/hr. The fed liquid was continuously distilled in the first distiller at a liquid temperature of 135° C. under a distiller top pressure of 10 mmHg at a reflux ratio of 2. A gas phase fraction consisting of 5.63% by weight of dimethyl oxalate, 61.48% by weight of methylphenyl oxalate, 30.43% by weight of phenol and 2.46% by weight of diphenyl oxalate was withdrawn at a rate of about 47 g/hr from the top portion of the first distiller, and condensed. Also, a liquid phase fraction comprising 97.9% by weight of diphenyl oxalate was withdrawn at a rate of 58 g/hr from the bottom portion of the first distiller.

To refine the liquid phase fraction withdrawn from the first distiller, the same type of glass distiller as the first distiller was used as a second distiller. In this second distiller, the liquid phase fraction of the first distiller was continuously distilled under the similar conditions as in the first distiller. A resultant gas phase fraction comprising 99.9% by weight or more of diphenyl oxalate was withdrawn at a flow rate of about 90 g/hr from the top portion of the second distiller and condensed. Also, a resultant liquid phase fraction containing about 15% by weight of tetraphenoxytitanium was withdrawn at a flow rate of about 15 g/hr from the bottom portion of the second distiller. The amount of the catalyst was determined by atomic absorption spectrometry.

Example 4 (Decarbonylation step (C))

A round flask having a capacity of 300 ml and equipped with a thermometer and a stirrer was charged with a reaction mixture consisting of 200 g (0.826 mole) of the refined diphenyl oxalate obtained in Example 3 and 1.55 g (0.0041 mole) of tetraphenylphosphonium chloride. The charged flask was heated by a mantle heater at a temperature of 250° C. for 2 hours to decarbonylate the diphenyl oxalate, while discharging a resultant by-product gas comprising carbon monoxide to the outside of the reaction system through an exhaust pipe connected to the flask.

The resultant liquid phase fraction remaining in the flask was subjected to gas chromatographic analysis. It was found that the resultant liquid phase fraction comprised 98.1% by weight of diphenyl carbonate and 1.1% by weight of diphenyl oxalate.

Thereafter, into the flask, a solution of 0.5 molar % of tetraphenylphosphonium chloride in the refined diphenyl oxalate obtained in Example 3 was continuously fed at a flow rate of 70 ml/hr, while withdrawing the resultant gas and liquid phase fractions from the flask so as to maintain the volume of the liquid phase fraction contained in the flask at a level of 200 ml, and while controlling the mantle heater so as to maintain the temperature of the liquid phase fraction at a level of 250° C.

When the composition of the liquid phase fraction in the flask is stabilized, namely about 10 hours after the start of the continuous reaction, the withdrawn liquid phase fraction was analyzed, as a result, it was found that the withdrawn liquid phase fraction comprised 91.2% by weight of diphenyl carbonate and 7.8% by weight of diphenyl oxalate. Also, the gas phase fraction comprising about 100% of carbon monoxide was withdrawn at a flow rate of about 110 ml/hr.

Example 5 (Collection step (D))

To refine and collect diphenyl carbonate, the same glass distiller as in Example 3 was used. The liquid phase fraction of Example 4 was continuously fed into and distilled in the distiller under the same conditions as in Example 3. From the top portion of the distiller, a resultant gas phase fraction was discharged and condensed by a cooler. The condensed liquid comprising 99.9% by weight or more of diphenyl carbonate was collected.

Example 6

The same liquid phase fraction as that obtained in the first distiller of Example 3 was fed into the same second glass distiller as the first distiller of Example 3 through an inlet located 80 cm below the top of the second distiller, at a flow rate of 100 ml/hr. In the second distiller, the fed liquid phase fraction was distillated at a liquid temperature of 180° C. under a distiller top pressure of 10 mmHg at a reflux ratio of 2. A resultant gas phase fraction was withdrawn from the top portion of the second distiller at a flow rate of about 90 g/hr, and condensed. The condensed liquid contained 99.7% by weight or more of diphenyl oxalate. Also, a resultant liquid phase fraction containing about 15% by weight of tetraphenoxytitanium was withdrawn from the bottom portion of the second distiller at a flow rate of about 15 g/hr.

The resultant condensed liquid was subjected to the same decarbonylation step (C) and the collection step (D) as in Examples 4 and 5. The final liquid phase fraction contained diphenyl carbonate in a degree of purity of 99.9% by weight or more.

Example 7

The same liquid phase fraction as in Example 2 was fed into a stainless steel (SUS)-made distiller packed with Helipack packings (5(D)×5(H) mm) and having an inner diameter of 30 mm and a height of 3 m, at a location of 1 m below the top of the distiller, at a feeding rate of 100 ml/hr.

The fed liquid phase fraction was continuously distilled at a liquid temperature of 198° C. under a distiller's top portion pressure of 10 mmHg at a reflux ratio of 0.5. From the top portion of the distiller, a resultant gas phase by-product fraction was withdrawn and condensed by a cooler and the condensed liquid was delivered at a flow rate of 44 ml/hr. The condensed liquid consisted of 6.38% by weight of dimethyl oxalate, 30.84% by weight of phenol, 62.78% by weight of methylphenyl oxalate. Also, from the portion of the distiller at a location of 50 cm above the bottom of the distiller, a gas phase main product fraction was withdrawn and condensed by a condenser, and the condensed liquid was delivered from the condenser at a flow rate of 55 g/hr. The condensed liquid contained diphenyl oxalate at a degree of purity of 99.2% by weight.

Further, from the bottom portion of the distiller, a liquid phase fraction containing tetraphenoxytitanium was withdrawn at a flow rate of about 5 g/hr.

The condensed diphenyl oxalate fraction was processed by the same decarbonylation step (C) and collection step (D) as in Example 4 and 5.

The final liquid phase fraction contained diphenyl carbonate at a degree of purity of 99.9% by weight or more.

Example 8

The same liquid phase fraction as that withdrawn from the second reactive distillation column of Example 2 was continuously fed into a rotation thin membrane-type evaporator having a heat-transfer area of 0.1 m$^2$ at a feeding rate of 100 ml/hr under a pressure of 20 mmHg. The evaporator was heated by a heating medium at a temperature of 200° C. to generate a vapor fraction containing dimethyl oxalate, phenol and methylphenyl oxalate.

From the bottom of the evaporator, a liquid phase fraction containing about 20% by weight of tetraphenoxytitanium was withdrawn at a flow rate of about 7 g/hr. The resultant vapor fraction was continuously fed into the same type of a first glass distiller as in Example 3 through an inlet located 80 cm below the top of the first distiller and distilled under the same conditions as in Example 3.

From the top portion of the first distiller, a resultant gas phase fraction was withdrawn and condensed. The condensed liquid comprised 6.52% by weight of dimethyl oxalate, 31.50% by weight of phenol, and 61.95% by weight of methylphenyl oxalate and was delivered at a flow rate of 43 ml/hr.

Also, from the bottom portion of the first distiller, a liquid phase fraction comprising diphenyl oxalate at a degree of purity of 99.6% by weight, at a flow rate of about 50 g/hr.

The liquid phase fraction withdrawn from the first distiller was fed into the same type of a second distiller as in Example 3 through an inlet located 80 cm below the top of the second distiller, at a flow rate of 100 ml/hr. The fed liquid phase fraction was continuously distilled at a liquid temperature of 178° C. under a distiller's top portion temperature of 10 mmHg at a recycling ratio of 2.

From the top portion of the second distiller, a resultant gas phase fraction was withdrawn and condensed. The condensed liquid contained 99.9% by weight or more of diphenyl oxalate and delivered at a flow rate of about 98 g/hr. Also, from the bottom portion of the second distiller, a resultant liquid fraction containing high boiling temperature compounds was withdrawn at a flow rate of about 7 g/hr.

The condensed liquid was subjected to the same decarbonylation step (C) and collection step (D) as in Example 4 and 5. In the final liquid phase fraction, the collected diphenyl carbonate had a degree of purity of 99.9% by weight or more.

Example 9

The same transesterification procedures as in Example 1 was carried out, except that a first solution consisting of 72.4% by weight of phenol, 27.0% by weight of dimethyl oxalate and 0.6% by weight of tetraphenoxytitanium was fed into a twelfth tray from the top of the same reactive distillation column as the first reactive distillation column in Example 1 at a flow rate of 143 ml/hr, and simultaneously a second solution comprising 2.3% by weight of methyl alcohol, 47.0% by weight of phenol and 45.2% by weight of dimethyl oxalate is fed into a fifteenth step from the top of the first reactive distillation column at a flow rate of 170 ml/hr.

The above-mentioned second solution was the condensation of the gas phase fraction delivered from the top portion of the second reactive distillation column in Example 2.

As a result, the resultant liquid phase fraction was withdrawn from the bottom portion of the reactive distillation column at a flow rate of about 307 g/hr and comprised 6.71% by weight of diphenyl oxalate, 26.51% by weight of methylphenyl oxalate, 23.63% by weight of dimethyl oxalate and 42.75% by weight of phenol. Also, the condensate of the resultant gas phase fraction was withdrawn from the top portion of the column at a flow rate of about 24 g/hr. This condensate consisted of 99.7% by weight of methyl alcohol and 0.3% by weight of dimethyl oxalate.

The liquid phase fraction was subjected to the same collection step (B), decarbonylation step (C) and collection step (D) as in Examples 3, 4 and 5. The final liquid phase fraction comprised diphenyl carbonate in a degree of purity of 99.9% by weight or more.

Example 10

The same first and second transesterification procedures as in Examples 1 and 2 were carried out except that 300 ml/hr of the liquid phase fraction delivered from the bottom portion of the first reaction distillation column of Example 1 and 50 ml/hr of the condensate of the gas phase fraction delivered from the top portion of the first distiller of Example 3 and containing methylphenyl oxalate were fed into the fifth step from the top of the second reactive distillation column.

The resultant liquid phase fraction was withdrawn at a flow rate of about 154 g/hr from the bottom portion of the second reactive distillation column and comprised 53.38% by weight of diphenyl oxalate, 25.92% by weight of methylphenyl oxalate, 2.22% by weight of dimethyl oxalate and 17.76% by weight of phenol. Also, from the top portion of the second column, a gas phase fraction comprising 2.35% by weight of methyl alcohol, 43,84% by weight of dimethyl oxalate, 50.16% by weight of phenol, 3.78% by weight of methylphenyl oxalate and 0.14% by weight of diphenyl oxalate was withdrawn and condensed at a flow rate of 220 g/hr.

The liquid phase fraction of the second reactive distillation column was subjected to the same collection, decarbonylation and collection steps (B), (C) and (D) as in Examples 3, 4 and 5.

The final liquid phase fraction contained 99.9% by weight or more of diphenyl carbonate.

In the process of the present invention, the diaryl carbonate having a high degree of purity can be continuously produced from the dialkyl oxalate and the phenol compound at a high yield, without using poisonous materials. During the process, the by-products to be discharged from the production system are only the corresponding alkyl alcohol and carbon monoxide, and the phenol compound and the intermediate products can be recycled and reused. Also, the collection and refining of the resultant diaryl carbonate can be effected easily. Therefore, the process of the present invention has a very high industrial applicability.

We claim:

1. A process for producing a diaryl oxalate comprising the step of:

(1) subjecting a dialkyl oxalate and a phenol compound to a first transesterification reaction in the presence of a transesterification catalyst in a first reactive distillation column, while evaporating away a reaction by-product comprising a corresponding alkyl alcohol from the first column;

(2) subjecting the reaction product mixture delivered from said first column to a second transesterification reaction in a second reactive distillation column, while evaporating away a reaction by-product comprising a corresponding dialkyl oxalate; and (3) distilling the reaction product mixture delivered from said second column, to collect the resultant diaryl oxalate.

2. The diaryl oxalate-producing process as claimed in claim 1, wherein the dialkyl oxalate is selected from those in which each alkyl group has 1 to 10 carbon atoms, and the phenol compound is selected from the group consisting of phenol and substituted phenols having at least one substituent selected from the group consisting of alkyl groups with 1 to 6 carbon atoms, alkoxyl groups with 1 to 6 carbon atoms, a nitro group, and halogen atoms.

3. The diaryl oxalate-producing process as claimed in claim 1, wherein the transesterification reaction in the step (1) is carried out at a temperature of 50° to 350° C. under a pressure of 133.32 mPa (0.001 mmHg) to 19.6133 Mpa (200 kg/cm$^2$).

4. The diaryl oxalate-producing process as claimed in claim 1, wherein the transesterification catalyst comprises at least one member selected from the group consisting of:

(1) alkali metal compounds, cadmium compounds and zirconium compounds;

(2) lead compounds (3) copper group metal compounds (4) iron compounds (5) zinc compounds (6) organic tin compounds, and (7) aluminum compounds, titanium compounds and vanadium compounds.

5. The diaryl oxalate-producing process as claimed in claim 1, wherein in the step (3), the diaryl oxalate is collected by a distillation of the reaction mixture delivered from the second column.

6. The diaryl oxalate-producing process as claimed in claim 1, wherein in the step (1), the starting material comprises a dialkyl oxalate and a phenol, and in the step (3), the resultant diphenyl oxalate is collected by subjecting the reaction product mixture of the step (2) to a crystallization procedure in which an adduct of diphenyl oxalate and phenol is crystallized and precipitated from the reaction product mixture, and heat-decomposing the adduct crystals, while evaporating away the resultant phenol from the heat-decomposition system.

7. The diaryl oxalate-producing process as claimed in claim 1, wherein in the step (1), a dialkyl oxalate, a phenol compound and a transesterification catalyst are fed into the first reactive distillation column, and the transesterification reaction of the alkyl oxalate with the phenol compound in the presence of the transesterification catalyst is carried out, while withdrawing a resultant first vapor phase fraction containing a corresponding alkyl alcohol from the top portion of the first column; in the step (2), a resultant liquid phase fraction of the step (1) containing an alkylaryl oxalate is fed, into the second trasesterification reaction to allow the alkylaryl oxalate contained liquid phase fraction to be transesterified into the corresponding diaryl oxalate and dialkyl oxalate, while withdrawing a resultant second vapor phase fraction containing the dialkyl oxalate from the top portion of the second column; and in the step (3), a resultant liquid phase fraction of the step (2) containing the diaryl oxalate is fed from the bottom portion of the second column into a distillation column and is distilled therein, and a resultant third vapor phase fraction of the step (3) comprising the distilled diaryl oxalate is withdrawn and collected from the distillation column.

8. The diaryl oxalate producing process as claimed in claim 1, wherein in the step (1), a dialkyl oxalate, a phenol compound and a transesterification catalyst are fed into the first reactive distillation column, and the transesterification reaction of the dialkyl oxalate with the phenol compound in the presence of the transesterification catalyst is carried out, while withdrawing a resultant first vapor phase fraction containing a corresponding alkyl alcohol from the top portion of the first column; in the step (2), a resultant liquid phase fraction of the step (1) containing an alkylaryl oxalate is fed from the bottom portion of the first column into the second reactive distillation column, and is subjected to the second transesterification reaction to allow the alkylaryl oxalate contained liquid phase fraction to be transesterified into corresponding diaryl oxalate and dialkyl oxalate, while withdrawing a resultant second vapor phase fraction containing the dialkyl oxalate from the top portion of the second column; and in the step (3), a resultant liquid phase fraction of the step (2) containing the diaryl oxalate is fed from the bottom portion of the second column into an evaporator and is evaporated therein, a resultant vapor phase fraction generated in the evaporator is fed from the evaporator into a first distiller and is distilled therein, while withdrawing a vapor phase fraction generated in the first distiller and containing the alkylaryl oxalate from the top portion of the first distiller, a resultant liquid phase fraction generated in the first distiller and containing the diaryl oxalate is fed from the bottom portion of the first distiller into a second distiller and is distilled therein, while withdrawing a vapor phase fraction generated in the first distiller and containing the alkylaryl oxalate from the top portion of the first distiller, a resultant liquid phase fraction generated in the first distiller and containing the diaryl oxalate is fed from the bottom portion of the first distiller into a second distiller and is distilled therein, and a resultant third vapor phase fraction generated in the second distiller and containing the diaryl oxalate is withdrawn and collected from the second distiller.

9. The diaryl oxalate-producing process as claimed in claim 1, wherein in the step (1), a dialkyl oxalate, a phenol compound and a transesterification catalyst are fed into the first reactive distillation column, and the transesterification reaction of the dialkyl oxalate with the phenol compound in the presence of the transesterification catalyst is carried out, while withdrawing a resultant first vapor phase fraction containing a corresponding alkyl alcohol from the top portion of the first column; in the step (2), a resultant liquid phase fraction of the step (1) containing an alkylaryl oxalate is fed from the bottom portion of the first column into the second reactive distillation column, and is subjected to the second transesterification reaction to allow the alkylaryl oxalate contained in the liquid phase fraction to be transesterified into the corresponding diaryl oxalate and dialkyl oxalate, while withdrawing a resultant second vapor phase fraction containing the dialkyl oxalate from the top portion of the second column; and in the step (3), a resultant liquid phase fraction of the step (2) containing the diaryl oxalate is fed from the bottom portion of the second column into a first distiller and is distilled therein, while withdrawing a resultant vapor phase fraction containing the alkylaryl oxalate from the top portion of the first distiller, a resultant liquid phase fraction generated in the first distiller and containing the diaryl oxalate is fed from the bottom portion of the first distiller into a second distiller and is distilled therein, and a resultant third vapor phase fraction generated in the second distiller and containing the diaryl oxalate is withdrawn and collected from the second distiller.

10. The diaryl oxalate-producing process as claimed in claim 7, wherein the second vapor phase fraction withdrawn from the second reactive distillation column and containing the dialkyl oxalate is recycled into the first reactive distillation column.

11. The diaryl oxalate-producing process as claimed in claim 8, wherein the second vapor phase fraction withdrawn from the second reactive distillation column and containing the dialkyl oxalate is recycled into the first reactive distillation column.

12. The diaryl oxalate-producing process as claimed in claim 9, wherein the second vapor phase fraction withdrawn from the second reactive distillation column and containing the dialkyl oxalate is recycled into the first reactive distillation column.

13. The diaryl oxalate-producing producing process as claimed in claims 8, wherein the vapor phase fraction withdrawn from the top portion of the first distiller and containing the alkylaryl oxalate or a condensation of the vapor phase fraction is recycled into the second reactive distillation column.

14. The diaryl oxalate-producing process as claimed in claim 9, wherein the vapor phase fraction withdrawn from the top portion of the first distiller and containing the alkylaryl oxalate or a condensation of the vapor phase fraction is recycled into the second reactive distillation column.

* * * * *